United States Patent
Zhang et al.

(10) Patent No.: US 11,969,368 B2
(45) Date of Patent: Apr. 30, 2024

(54) LUMEN STENT AND PREFORM THEREOF, AND METHODS FOR PREPARING THE LUMEN STENT AND PREFORM THEREOF

(71) Applicant: BIOTYX MEDICAL (SHENZHEN) CO., LTD., Guangdong (CN)

(72) Inventors: Deyuan Zhang, Shenzhen (CN); Xianmiao Chen, Shenzhen (CN); Wenjiao Lin, Shenzhen (CN); Xiangdong Liu, Shenzhen (CN)

(73) Assignee: BIOTYX MEDICAL (SHENZHEN) CO., LTD., Shenzhen (CN)

(*) Notice: Subject to any disclaimer, the term of this patent is extended or adjusted under 35 U.S.C. 154(b) by 0 days.

(21) Appl. No.: 17/859,563

(22) Filed: Jul. 7, 2022

(65) Prior Publication Data
US 2022/0339012 A1    Oct. 27, 2022

Related U.S. Application Data

(62) Division of application No. 15/526,509, filed on May 12, 2017, now Pat. No. 11,389,308.

(51) Int. Cl.
*A61F 2/82* (2013.01)
*A61L 27/04* (2006.01)
(Continued)

(52) U.S. Cl.
CPC ............. *A61F 2/82* (2013.01); *A61L 27/04* (2013.01); *A61L 31/02* (2013.01); *A61L 31/022* (2013.01);
(Continued)

(58) Field of Classification Search
CPC ...... A61F 2/82; A61F 2/86; A61F 2/92; A61F 2310/00017; A61F 2210/004;
(Continued)

(56) References Cited

U.S. PATENT DOCUMENTS 3,986,867 A * 10/1976 Masumoto .............. C22C 45/02
420/583
5,593,513 A *  1/1997 Ramanan ................ C22C 45/02
148/307
(Continued)

FOREIGN PATENT DOCUMENTS

CN       103371876 A * 10/2013 ............... A61F 2/86

*Primary Examiner* — Seema Mathew
(74) *Attorney, Agent, or Firm* — Raymond Sun

(57) ABSTRACT

A lumen stent preform is provided using a plasma nitriding technology, a preparation method thereof, a method for preparing a lumen stent by using the preform, and a lumen stent obtained according to the method. The preform is manufactured by using pure iron or an iron alloy containing no strong nitrogen compound, has a hardness of 160-250HV0.05/10, and has a microstructure that is a deformed structure having a grain size scale greater than or equal to 9 or a deformed structure after cold machining. Alternatively, the preform is an iron alloy containing a strong nitrogen compound, and has a microstructure that is a deformed structure having a grain size scale greater than or equal to 9 or a deformed structure after cold machining. The lumen
(Continued)

stem preform meets the requirements of a conventional stent for radial strength and plasticity, so that plasma nitriding is applicable to commercial preparation of a lumen stent.

20 Claims, 4 Drawing Sheets

(51) Int. Cl.
A61L 31/02 (2006.01)
C21D 8/10 (2006.01)
C21D 9/08 (2006.01)
C22C 38/00 (2006.01)
C22C 38/02 (2006.01)
C22C 38/04 (2006.01)
C22C 38/14 (2006.01)
C22C 38/42 (2006.01)
C22C 38/44 (2006.01)
C23C 8/02 (2006.01)
C23C 8/26 (2006.01)
B21C 1/00 (2006.01)
B21C 1/24 (2006.01)

(52) U.S. Cl.
CPC ............... *C21D 8/105* (2013.01); *C21D 9/08* (2013.01); *C22C 38/002* (2013.01); *C22C 38/02* (2013.01); *C22C 38/04* (2013.01); *C22C 38/14* (2013.01); *C22C 38/42* (2013.01); *C22C 38/44* (2013.01); *C23C 8/02* (2013.01); *C23C 8/26* (2013.01); *A61F 2240/001* (2013.01); *B21C 1/00* (2013.01); *B21C 1/003* (2013.01); *B21C 1/24* (2013.01)

(58) Field of Classification Search
CPC ..... A61F 2240/001; A61F 2310/00011; A61L 31/022; C22C 45/02; B21C 1/24; B21C 1/003
See application file for complete search history.

(56) References Cited

U.S. PATENT DOCUMENTS

| | | | |
|---|---|---|---|
| 5,871,593 A * | 2/1999 | Fish | H01F 1/15308 148/307 |
| 5,891,191 A * | 4/1999 | Stinson | A61L 31/022 623/1.2 |
| 2003/0018380 A1* | 1/2003 | Craig | C22C 38/58 623/924 |
| 2004/0000361 A1* | 1/2004 | Trozera | A61L 31/022 148/593 |
| 2004/0129347 A1* | 7/2004 | Craig | C22C 38/30 148/325 |
| 2005/0131522 A1* | 6/2005 | Stinson | B23K 26/324 623/901 |
| 2009/0165898 A1* | 7/2009 | Wong | A61L 31/022 623/1.18 |
| 2010/0092329 A1* | 4/2010 | Branagan | C22C 1/11 164/47 |
| 2010/0174367 A1* | 7/2010 | Janko | C22C 38/44 206/363 |
| 2015/0182674 A1* | 7/2015 | Schaffer | C21D 9/525 29/520 |
| 2018/0221536 A1* | 8/2018 | Chen | A61L 31/022 |
| 2020/0390943 A1* | 12/2020 | Lin | A61L 31/148 |

* cited by examiner

Table 5 Microscopic grain size relationship of arbitrary orientation、 uniform and equiaxed grains

| Micro-grain Size Number G | Number of grains per square millimeter $n_a$ | Average cross-sectional area of grain $\bar{a}$ | | Average diameter $\bar{d}$ | | Average intercept $\bar{l}$ | | Number of point per mm |
|---|---|---|---|---|---|---|---|---|
| | $1/mm^2 (1\times)$ | $mm^2$ | $\mu m^2$ | mm | $\mu m$ | mm | $\mu m$ | $1/mm$ $(1\times)$ |
| 00 | 3.88 | 0.2581 | 258064 | 0.5080 | 508.0 | 0.4525 | 452.5 | 2.21 |
| 0 | 7.75 | 0.1290 | 129032 | 0.3592 | 359.2 | 0.3200 | 320.0 | 3.12 |
| 0.5 | 10.96 | 0.0912 | 91239 | 0.3021 | 302.1 | 0.2691 | 269.1 | 3.72 |
| 1.0 | 15.50 | 0.0645 | 64516 | 0.2540 | 254.0 | 0.2263 | 226.3 | 4.42 |
| 1.5 | 21.92 | 0.0456 | 45620 | 0.2136 | 213.6 | 0.1903 | 190.3 | 5.26 |
| 2.0 | 31.00 | 0.0323 | 32258 | 0.1796 | 179.6 | 0.1600 | 160.0 | 6.25 |
| 2.5 | 43.84 | 0.0228 | 22810 | 0.1510 | 151.0 | 0.1345 | 134.5 | 7.43 |
| 3.0 | 62.00 | 0.0161 | 16129 | 0.1270 | 127.0 | 0.1131 | 113.1 | 8.84 |
| 3.5 | 87.68 | 0.0114 | 11405 | 0.1068 | 106.8 | 0.0951 | 95.1 | 10.51 |
| 4.0 | 124.00 | 0.00806 | 8065 | 0.0898 | 89.8 | 0.0800 | 80.0 | 12.50 |
| 4.5 | 175.36 | 0.00570 | 5703 | 0.0755 | 75.5 | 0.0673 | 67.3 | 14.87 |
| 5.0 | 248.00 | 0.00403 | 4032 | 0.0635 | 63.5 | 0.0566 | 56.6 | 17.68 |
| 5.5 | 350.73 | 0.00285 | 2851 | 0.0534 | 53.4 | 0.0476 | 47.6 | 21.02 |
| 6.0 | 496.00 | 0.00202 | 2016 | 0.0449 | 44.9 | 0.0400 | 40.0 | 25.00 |
| 6.5 | 701.45 | 0.00143 | 1426 | 0.0378 | 37.8 | 0.0336 | 33.6 | 29.73 |
| 7.0 | 992.00 | 0.00101 | 1008 | 0.0318 | 31.8 | 0.0283 | 28.3 | 35.36 |
| 7.5 | 1402.9 | 0.00071 | 713 | 0.0267 | 26.7 | 0.0238 | 23.8 | 42.04 |
| 8.0 | 1984.0 | 0.00050 | 504 | 0.0225 | 22.5 | 0.0200 | 20.0 | 50.00 |
| 8.5 | 2805.8 | 0.00036 | 356 | 0.0189 | 18.9 | 0.0168 | 16.8 | 59.46 |
| 9.0 | 3968.0 | 0.00025 | 252 | 0.0156 | 15.9 | 0.0141 | 14.1 | 70.71 |
| 9.5 | 5611.6 | 0.00018 | 178 | 0.0133 | 13.3 | 0.0119 | 11.9 | 84.09 |
| 10.0 | 7936.0 | 0.00013 | 126 | 0.0112 | 11.2 | 0.0100 | 10.0 | 100.0 |
| 10.5 | 11223.2 | 0.000089 | 89.1 | 0.0094 | 9.4 | 0.0084 | 8.4 | 118.9 |
| 11.0 | 15872.0 | 0.000063 | 63.0 | 0.0079 | 7.9 | 0.0071 | 7.1 | 141.4 |
| 11.5 | 22446.4 | 0.000045 | 44.6 | 0.0067 | 6.7 | 0.0060 | 5.9 | 168.2 |
| 12.0 | 31744.1 | 0.000032 | 31.5 | 0.0056 | 5.6 | 0.0050 | 5.0 | 200.0 |
| 12.5 | 44892.9 | 0.000022 | 22.3 | 0.0047 | 4.7 | 0.0042 | 4.2 | 237.8 |
| 13.0 | 63488.1 | 0.000016 | 15.8 | 0.0040 | 4.0 | 0.0035 | 3.5 | 282.8 |
| 13.5 | 89785.8 | 0.000011 | 11.1 | 0.0033 | 3.3 | 0.0030 | 3.0 | 336.4 |
| 14.0 | 126976.3 | 0.000008 | 7.9 | 0.0028 | 2.8 | 0.0025 | 2.5 | 400.0 |

FIG. 9

LUMEN STENT AND PREFORM THEREOF, AND METHODS FOR PREPARING THE LUMEN STENT AND PREFORM THEREOF

TECHNICAL FIELD

The present invention relates to the field of interventional medical instruments, and in particular, to a lumen stent and a lumen stent preform, and preparation methods thereof.

BACKGROUND ART

Currently, implantable medical devices are generally made of metals and alloys thereof, ceramics, polymers and related composites, where metal-based implantable medical devices are very popular due to their superior mechanical properties, such as high strength and high toughness.

Iron, as an important element for human body, is involved in many biochemical processes, such as oxygen transport. As provided by Peuster M et al., a perishable and pure iron stent that is made by laser engraving and has a shape similar to clinically used metal stents is implanted to the descending aortas of 16 New Zealand rabbits. The animal experimental results show that there are neither thrombosis complications nor adverse events within 6-18 months, and the pathological examination shows that there is no inflammatory reaction in partial vessel walls, and no obvious proliferation of smooth muscle cells. These results preliminarily prove that the degradable iron stent is safe and reliable and has good application prospects. However, this study also finds that the pure iron stent has a slower corrosion rate in vivo environment. In addition, it has been reported that the radial strength and longitudinal compressive strength of an iron-based stent are similar to those of a stainless steel stent and a cobalt chromium stent, but the pure-iron stent has a lower mechanical property.

In order to improve the mechanical property of the iron-based stent, the current researches mainly focus on the development of new-type iron alloys, new preparation methods for iron materials, or the preparation of iron alloy layers on pure iron surface and the modification of pure iron materials. We have found that the nitriding treatment on pure iron/iron alloys can, on one hand, improve the stent strength (characterized by hardness or radial strength) to reduce material consumption, and on the other hand, can increase the corrosion rate of pure iron/iron alloys to shorten the stent absorption cycle. In addition, the nitriding treatment will not significantly reduce the plasticity of the material when increasing the strength and hardness of the pure iron/iron alloys at the same time, and the implantable medical device components made of nitrided iron alloys can withstand the expansion deformation in use and prevent breakage.

The existing nitriding methods include gas nitriding, salt-bath nitriding, and plasma nitriding. The gas nitriding and salt-bath nitriding methods have no special requirements for microstructure and original hardness of raw materials of stents, but the gas nitriding method takes too much time for modification treatment and has very low production efficiency, so that it is difficult to carry out large-scale use in actual production. The salt-bath nitriding method requires a large amount of highly-toxic molten cyanide salts for nitriding treatment, which causes high risk in clinical application in terms of high-risk third-class implantable medical device products (such as bioabsorbable vascular stents). Further, the compound layers on the surfaces of samples obtained through the gas nitriding and salt-bath nitriding treatments are generally very thick (≥0.01 mm), which is unfavorable for the subsequent polishing and fine structure design of thin-wall (wall thickness≤0.12 mm) and complicated hollowed medical devices or components thereof.

The plasma nitriding method has high nitriding efficiency, which uses nitrogen and hydrogen as treatment gas without introducing any other toxic substances, and ensures that the compound layers (commonly known as white bright layers, nitrogen compound layers) obtained through nitriding are usually thin and discontinuous, and there is also no compound layer by controlling the parameters of plasma nitriding process, thereby greatly facilitating the subsequent polishing treatment and leaving room for the subsequent fine structure design of medical devices. However, not all iron-based materials are suitable for the preparation of lumen stents by nitriding. For conventional lumen stents, the requirements for both radial strength and plasticity are satisfied. For example, for coronary stents, it is required that the radial strength is at least 80 kPa and the over-plasticity (that is, plasticity) is at least 20%, and for peripheral stents, it is required that the radial strength is at least 50 kPa and the over-plasticity (that is, plasticity) is at least 20%. Therefore, it is necessary to provide a lumen stent preform that is not only advantageous for nitriding but also ensures that a prepared lumen stent after nitriding satisfies the requirements for both radial strength and plasticity.

SUMMARY OF THE INVENTION

The technical problem to be solved by the present invention is to provide a lumen stent preform and a lumen stent, and preparation methods thereof, to overcome the defects in the prior art.

Solutions to the Problem

Technical Solutions

The present invention provides a lumen stent preform, which is made of pure iron or an iron alloy, and where a total impurity element content of the pure iron is less than or equal to 0.5 wt. %, a total alloy element content of the iron alloy is less than or equal to 3 wt. %, the iron alloy contains no strong nitride-forming element, the lumen stent preform has a hardness of 160-250HV0.05/10, and has a microstructure that is a deformed structure having a grain size number greater than or equal to 9 or a deformed structure after cold machining.

In the lumen stent preform of the present invention, the lumen stent preform has a hardness of 200-250HV0.05/10, and has a microstructure that is a deformed structure after cold machining.

In the lumen stent preform of the present invention, a carbon content in the total impurity elements of the pure iron is less than or equal to 0.022%, and a carbon content in the total alloy elements of the iron alloy is less than or equal to 0.45 wt. %.

In the lumen stent preform of the present invention, the lumen stent preform has an outer diameter of 1.2-4.2 mm and a wall thickness of 0.08-0.24 mm.

The present invention provides a lumen stent preform, where the lumen stent preform is an iron alloy containing at least one strong nitride-forming element, a total alloy element content of the iron alloy is less than or equal to 3 wt. %, and a total content of the strong nitride-forming element is greater than or equal to 0.05 wt. %; and the lumen stent preform has a microstructure that is a deformed structure having a grain size number greater than or equal to 9 or a deformed structure after cold machining.

In the lumen stent preform of the present invention, the strong nitride-forming element includes at least one of Ti, Cr, Al, Zr, Nb, V, B, W, and Mo.

In the lumen stent preform of the present invention, a carbon content in the total alloy elements of the iron alloy is less than or equal to 0.45 wt. %.

In the lumen stent preform of the present invention, the lumen stent preform has an outer diameter of 1.2-4.2 mm and a wall thickness of 0.08-0.24 mm.

The present invention provides a method for preparing a lumen stent preform, including drawing a blank into the above lumen stent preform.

In the method for preparing a lumen stent preform of the present invention, the blank is pure iron having a total impurity element content of less than or equal to 0.5 wt. %; or an iron alloy having a total alloy element content of less than or equal to 3 wt. % and containing no strong nitride-forming element; or an iron alloy in which a total alloy element content is less than or equal to 3 wt. % and a total content of strong nitride-forming elements is greater than or equal to 0.05 wt. %.

In the method for preparing a lumen stent preform of the present invention, a carbon content in the total impurity elements of the pure iron is less than or equal to 0.022%, and a carbon content in the total alloy elements of the iron alloy is less than or equal to 0.45 wt.

In the method for preparing a lumen stent preform according to claim 10, the strong nitride-forming element includes at least one of Ti, Cr, Al, Zr, Nb, V, B, W, and Mo.

In the method for preparing a lumen stent preform of the present invention, the preparation method further includes processing the blank into a completely annealed structure or an incompletely annealed structure before drawing the blank.

In the method for preparing a lumen stent preform of the present invention, the drawing passes of the drawing include at least one time of drawing with a mandrel and one time of drawing without a mandrel.

In the method for preparing a lumen stent preform of the present invention, when the blank is the above pure iron or the above iron alloy containing no strong nitride-forming element, the drawing without a mandrel is the last pass in the drawing, and when the blank is the above iron alloy containing a strong nitride-forming element, an annealing pass is further included after the drawing without a mandrel.

In the method for preparing a lumen stent preform of the present invention, the drawing with a mandrel has a drawing coefficient of 1.2-2.5.

In the method for preparing a lumen stent preform of the present invention, the drawing with a mandrel has a drawing coefficient of 1.5-2.0.

In the method for preparing a lumen stent preform of the present invention, the drawing without a mandrel has a drawing coefficient of about 1 or slightly greater than 1.

In the method for preparing a lumen stent preform of the present invention, the drawing with a mandrel is drawing with a long mandrel.

In the method for preparing a lumen stent preform of the present invention, the drawing passes are implemented at a recrystallization temperature of the blank.

In the method for preparing a lumen stent preform of the present invention, an annealing pass is supplemented between the drawing passes.

In the method for preparing a lumen stent preform of the present invention, when the blank has a hardness of 200-240HV0.05/10, an annealing pass is supplemented before the drawing pass with a mandrel, and the annealing temperature is 400-650° C.

In the method for preparing a lumen stent preform of the present invention, when a lumen stent preform with hardness less than 250HV0.05/10 is to be manufactured, an annealing pass is further supplemented between the drawing passes, and the annealing temperature is 400-650° C.

The present invention provides a method for preparing a lumen stent, including drawing a blank into the above lumen stent preform, where the blank is pure iron having a total impurity element content of less than or equal to 0.5 wt. %, or an iron alloy having a total alloy element content of less than or equal to 3 wt. % and containing no strong nitride-forming element, or an iron alloy in which a total alloy element content is less than or equal to 3 wt. % and a total content of strong nitride-forming elements is greater than or equal to 0.05 wt. %.

In the method for preparing a lumen stent of the present invention, the preparation method further includes manufacturing the lumen stent preform into an initial stent, heating the initial stent up to 320-560° C., and performing plasma nitriding on the initial stent for 15-180 min at an air pressure of 10-500 Pa and a bias voltage of 500-700V.

In the method for preparing a lumen stent of the present invention, when the lumen stent preform has a hardness of 200-250HV0.05/10 and a microstructure that is a deformed structure after cold machining, the preparation method further includes manufacturing the lumen stent preform into an initial stent, heating the initial stent up to 320-420° C., and performing plasma nitriding on the initial stent for 30-180 min at air pressure of 50-500 Pa and a bias voltage of 500-700V.

In the method for preparing a lumen stent of the present invention, a flow ratio of nitrogen to hydrogen in the gas source in the plasma nitriding is 1:1 to 1:3.

In the method for preparing a lumen stent of the present invention, the preparation method further includes performing polishing after plasma nitriding to obtain the lumen stent.

The present invention provides a lumen stent, where the lumen stent is obtained by the preparation method described above, and has a hardness of 250-350HV0.05/10 and a microstructure that is a deformed structure having a grain size number greater than or equal to 9 or a deformed structure after cold machining.

In the lumen stent of the present invention, when the lumen stent preform has a hardness of 200-250HV0.05/10 and a microstructure that is a deformed structure after cold machining, the hardness of the lumen stent is 300-350HV0.05/10 and the microstructure is a deformed structure after cold machining.

In the lumen stent of the present invention, the lumen stem has radial strength of 80-260 kPa and over-plasticity of 20-50% or radial strength of 50-130 kPa and over-plasticity of 20-50%.

In the lumen stent of the present invention, the lumen stent has radial strength of 80-260 kPa and over-plasticity of 20-40% or radial strength of 50-130 kPa and over-plasticity of 20-40%.

In the lumen stent of the present invention, a corrosion rate during in-vitro soaking of the lumen stent is 0.25-1.5 times higher than that of the initial stent.

In the lumen stent of the present invention, a corrosion rate during in-vitro soaking of the lumen stent is 1-1.5 times higher than that of the initial stent.

In the lumen stent of the present invention, the lumen stent has a metal coverage of 11-16% or 7-11%.

In the lumen stent of the present invention, the lumen stent includes a solid solution and an iron-nitrogen compound; or the lumen stent includes a solid solution, an iron-nitrogen compound, and a compound composed of a strong nitride-forming element and nitrogen.

In the lumen stent of the present invention, the lumen stent includes, sequentially from surface to inside, a first laminated structure and a second laminated structure, where the first laminated structure includes a solid solution and an iron-nitrogen compound, and the second laminated structure includes a solid solution; or the first laminated structure includes a solid solution, an iron-nitrogen compound, and a compound composed of a strong nitride-forming element and nitrogen, and the second laminated structure includes a solid solution.

In the lumen stent of the present invention, the lumen stent includes, sequentially from surface to inside, a first laminated structure, a second laminated structure, and a third laminated structure, where the first laminated structure includes a solid solution and an iron-nitrogen compound, the second laminated structure includes a solid solution, and the third laminated structure is an iron core layer; or the first laminated structure includes a solid solution, an iron-nitrogen compound, and a compound composed of a strong nitride-forming element and nitrogen, the second laminated structure includes a solid solution, and the third laminated structure is an iron core layer.

Advantageous Effects of the Invention

Advantageous Effects

The technical solution adopted by the present invention to solve the technical problem is to use an iron-based lumen stent preform that has a hardness of 160-250HV0.05/10 and a microstructure that is a deformed structure having a grain size number greater than or equal to 9 or a deformed structure after cold machining. Alternatively, an iron alloy lumen stent preform that has a microstructure that is a deformed structure having a grain size number greater than or equal to 9, or a deformed structure after cold machining and containing a strong nitride-forming element can be used. The two lumen stent preforms described above are both suitable for plasma nitriding, and an applied temperature range during plasma nitriding is relatively large. In addition, the radial strength and plasticity of a lumen stent prepared therefrom satisfy the requirements of lumen stent products; therefore, the plasma nitriding technology can be commercially applicable to the preparation of lumen stents.

BRIEF DESCRIPTION OF THE DRAWINGS

The present invention will be further described with reference to the accompanying drawings and embodiments, and in the FIGS.:

FIG. 9 is a table illustrating the microscopic grain size relationship of arbitrary orientation, uniform, and equiaxed grains.

PREFERRED EMBODIMENTS FOR IMPLEMENTING THE INVENTION

Preferred Embodiments of the Invention

The present invention provides a lumen stent preform and a preparation method thereof favorable for plasma nitriding, a method for preparing a lumen stent satisfying the requirements for mechanical property of conventional lumen stents by using the preform, and a lumen stent obtained according to the method. In terms of the mechanical property, for a coronary stent, if an OD (outer diameter) is in a range of 2.0-5.0 mm, the radial strength of the coronary stent should not be less than 80 kPa, and over-plasticity should not be less than 20%. For a peripheral stent, if an OD is in a range of 5.0-14.0 mm, the radial strength of the peripheral stent should not be less than 50 kPa, and over-plasticity should not be less than 20%. The over-plasticity of 20% means that a stent rod will not crack or break when the outer diameter of a lumen stent is maximally expanded in clinical use by more than 20% of the nominal diameter of the stent. For clear understanding of the technical features, objectives, and advantages of the present invention, specific embodiments of the invention are now described in detail in accordance with the accompanying drawings.

Figure 1:
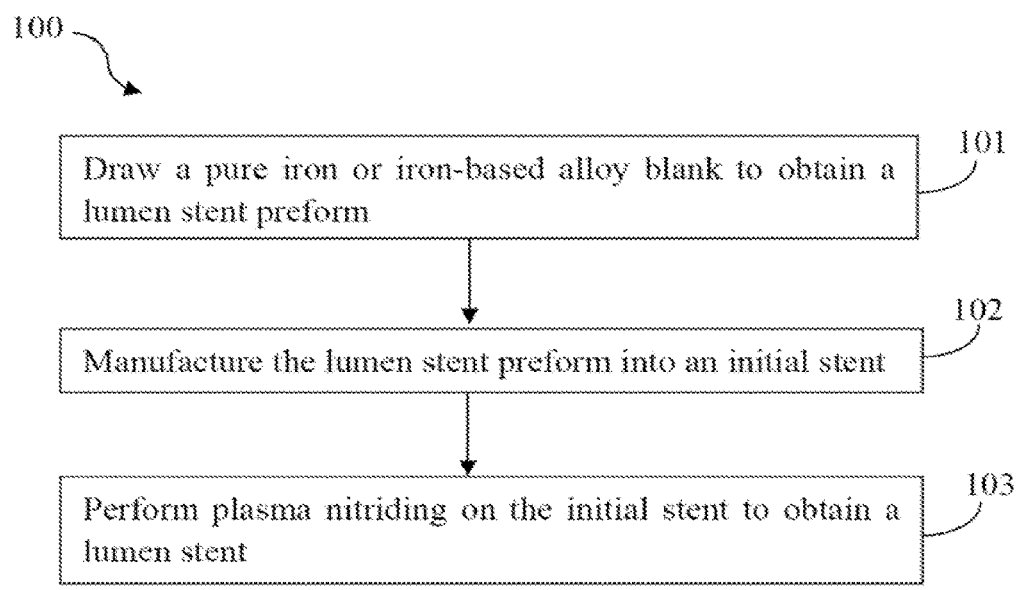
FIG. 1 is a flowchart of a method for preparing a lumen stent according to an embodiment of the present invention.

Referring to FIG. 1, a preparation method 100 of a lumen stent of the invention includes: Step 101: Draw a pure iron or iron alloy blank to obtain a lumen stent preform; Step 102: Manufacture the lumen stent preform into an initial stent; Step 103: Perform plasma nitriding on the initial stent to obtain a lumen stent. The lumen stent includes, but is not limited to, a vascular stent, an esophageal stent, and a tracheal stent.

In step 101, the blank is made of pure iron or an iron alloy (also referred to as an iron-based alloy), where a total impurity element content of the pure iron is less than or equal to 0.5 wt. %, and a total alloy element content of the iron alloy is less than or equal to 3 wt. %. As an implementation manner of the present invention, a carbon content in the total impurity elements of the pure iron is less than or equal to 0.022%, or a carbon content in the total alloy elements of the iron alloy is less than or equal to 0.45 wt. %. The iron alloy includes an iron alloy containing a strong nitride-forming element and an iron alloy containing no strong nitride-forming element, and all alloying elements of the iron alloy containing a strong nitride-forming element may contain one or more strong nitride-forming elements, where a total content of strong nitride-forming elements is greater than or equal to 0.05 wt. %, and the strong nitride-forming element includes, but is not limited to, Ti, Cr, Al, Zr, Nb, V, B, W, and Mo.

Drawing means that at a recrystallization temperature of tube blanks (for example at room temperature), an external force is applied to a front end of a tube to be drawn to draw the tube out from a die orifice having a smaller diameter than the tube, to obtain the tube having smaller diameter. In the present invention, a thin-wall tubular blank (hereinafter referred to as a tube blank) is drawn to obtain a lumen stent preform, so as to control the microstructure and hardness of the lumen stent preform. In practice, according to the teachings of the present invention, depending on the radial dimension of a lumen stent to be produced and the drawing parameters to be adopted in the drawing process, for example the number of drawing passes and/or drawing coefficients, an appropriate mold is selected, and is not described in greater detail herein.

Before the drawing, a step of treating the blank into an incompletely annealed structure or a completely annealed structure (an equiaxial structure) may be included. Generally, insulation treatment is performed on the blank at an annealing temperature of 570-700° C. for 0.5-2 h to achieve complete annealing, so that the blank forms a completely annealed structure, and insulation treatment is performed on the blank at a lower annealing temperature (for example, 400-550° C.) for a shorter period of time (for example, 0.5-1 h) to achieve incomplete annealing. The completely annealed structure and the incompletely annealed structure are both drawn by the same or similar drawing process, for example, having the same drawing coefficient and numbers of drawing passes. For example, in one embodiment, if the blank is a completely annealed structure, the hardness of pure iron may be about 901-HV0.05/10, and the hardness of an iron alloy may be 100-150HV0.05/10, the microstructures are both equiaxed grains having a grain size number greater than or equal to 4. Accordingly, an optional dimension may be as follows: a wall thickness is 0.16-3 mm, and an outer diameter is 3.5-20 mm. If the blank is an incompletely annealed structure, the hardness is higher than that of a blank that is a completely annealed structure having corresponding components, for example, the hardness of pure iron is typically greater than 90HV0.05/10, being 100 or 120HV0.05/10 or even more, and the hardness of the iron alloy is at least greater than 110HV0.05/10, the microstructures are both a deformed structure. Accordingly, an optional dimension may be as follows: a wall thickness is 0.13-3 mm, and an outer diameter is 2.3-20 mm. It should be noted that the blank features enumerated here are only examples, and not to be construed as a limitation to the present invention, those skilled in the art can select any suitable blanks as needed based on the teachings of the present invention.

The drawing passes in the drawing include at least one time of drawing with a mandrel and at least one time of drawing without a mandrel following the drawing with a mandrel, and the drawing with a mandrel may be drawing with a long mandrel. The drawing coefficient used in each procedure of drawing with a mandrel is $\mu=1.2$-$2.5$, and is $\mu=1.5$-$2.0$ in the embodiment of the present invention, where $\mu=Q0/Q1$, Q0 is a cross-sectional area of an original tube before drawing, and Q1 is a cross-sectional area of a tube preform obtained after drawing. The drawing coefficient is also referred to as extension coefficient when the drawing coefficient is characterized by a length of the tube. It should be understood that, for a solid component, a volume is unchanged before and after the drawing, so that the cross-sectional area ratio is inversely proportional to the length ratio.

After drawing with a mandrel, the mandrel and the tube blank are bonded together, thus there is a need for demolding to separate the mandrel from the tube blank. The demolding includes squeezing the blank to cause plastic deformation of the tube blank, and the mandrel does not deform due to relatively higher hardness, causing the mandrel to separate from the blank. As the blank undergoes plastic deformation after drawing with a mandrel, the surface condition and outer diameter of the blank are changed, thus there is a need for at least one time of drawing without a mandrel to fix the diameter (accurately fix the outer diameter) and eliminate deformation traces on the surface of the tube after demolding. Generally, the drawing coefficient used in the drawing without a mandrel is about 1.0, or slightly greater than 1.0, for example, may be 1.01-1.05, so as to reduce the outer diameter and increase the wall thickness of the tube blank by the drawing without a mandrel. If the blank is pure iron or the iron alloy containing no strong nitride-forming element described above, the drawing without a mandrel is the last pass in the drawing, that is, after the drawing without a mandrel, the entire drawing procedure is completed. When the blank is the iron alloy containing a strong nitride-forming element, the drawing without a mandrel may be followed by annealing to completely or incompletely anneal the blank, and the annealing temperature and time depend on the materials. For example, insulation treatment is performed on the blank at an annealing temperature of 570-700° C. for 0.5-2 h to achieve complete annealing; or insulation treatment is performed on the blank at a lower annealing temperature (for example 400-550° C.) for a shorter period of time (for example 0.5-1 h) to achieve incomplete annealing.

For example, 3-5 passes of drawing with a long mandrel and the last one pass of drawing without a mandrel may be adopted, optionally, 0-5 passes of annealing may be supplemented during the drawing passes. If a lumen stent preform with hardness of 250HV0.05/10 or more is needed, the annealing pass is not set in the drawing process. If a lumen stent preform with hardness less than 250HV0.05/10 is needed, several annealing passes may be supplemented in the drawing process. The timing of annealing depends on the hardness of the tube obtained in the intermediate drawing passes, and if the hardness of the tube obtained in the intermediate drawing passes is in a range of 200-240HV0.05/10, the annealing pass may be provided, with an annealing temperature being 400-650° C.

The outer diameter (OD) of the lumen stent preform obtained by drawing is 1.2-4.2 mm, and the wall thickness is 0.08-0.24 mm, in terms of mechanical property, the hardness is 160-250HV0.05/10 (Vickers hardness measured under 0.05 kg test force for 10 s), and in terms of a microstructure or a microscopic structure, the lumen stent preform has a grain size number greater than or equal to 9, or has a deformed structure after cold machining (cold-deformed structure for short). In one embodiment, the hardness of the lumen stent preform is 200-250HV0.05/10, and the microstructure is a deformed structure after cold machining. The lumen stent preform is of the same material as the blank, for example, if the blank is the iron alloy containing a strong nitride-forming element, the lumen stem preform obtained by drawing is of the iron alloy containing the strong nitride-forming element, where the hardness (Vickers hardness) is detected according to the test method in the standard GB/T 4340.1-2009, that is, the hardness (Vickers hardness) is calculated according to an indentation diagonal length by means of load of 50 gf and maintaining the pressure for 10 s.

Higher hardness of the lumen stent preform indicates that the nitriding is more favorable, and the nitriding can significantly improve material hardness. However, high hardness may lead to hardening of cold machining and scarification of the plasticity of materials, which in turn leads to the decrease of flexibility and fracture resistance of the obtained lumen stent with the increase of cold-machining hardening degree, and the higher the hardness, the greater the probability and degree that the lumen stent preform will be recovered and annealed during subsequent nitriding. The lumen stent preform prepared in the present invention has the hardness of 160-2501-HV0.05/10 and a microstructure that has a grain size number greater than or equal to 9 or is a deformed structure after cold machining, which is not only advantageous for the implementation of subsequent nitriding process, but also satisfies the requirements for both radial strength (hardness) and plasticity. In another aspect, the present invention also provides a lumen stent preform made of an iron alloy containing a strong nitride-forming element, the strong nitride-forming element is more easily bonded with nitrogen to form a compound having a microstructure which has a grain size number greater than or equal to 9 or is a deformed structure after cold machining, which is not only advantageous for the implementation of subsequent nitriding process, but also satisfies the requirements for both radial strength (hardness) and plasticity, as described below in detail.

The microstructure may be detected in the following manner, for example, a sample to be tested is cut first (such as a lumen stent preform or lumen stent), and the sample is embedded in resin by pouring resin into the sample. The resin sample is polished with sandpaper and velvet cloth to remove scratches on the cross section. Then the sample is eroded with 3-4% nitric acid alcohol solution for about 5-40 s. The sample is observed under a high-power microscope of at least 500 times magnification to detect the metallurgical structure. If the metallographic structure is found to be an equiaxed crystal structure, the grain size number of the material is evaluated according to the linear intercept method in the national standard GB/T 6394-2002. If the metallographic structure is a deformed structure, there is no need to calculate the grain size number.

In step 102, the lumen stent preform obtained in step 101 is manufactured into an initial stent. For example, the lumen stent preform is cut according to a preset stent pattern, followed by washing, to obtain the initial stent.

In step 103, the lumen stent preform obtained in step 102 is subjected to plasma nitriding to obtain a lumen stent. In one embodiment of the present invention, the initial stent is subjected to plasma nitriding at 320-560° C. (also referred to as nitriding temperature) under conditions of a bias voltage of 500-700V, total gas pressure of 10-500 Pa, and a flow ratio of nitrogen to hydrogen in the gas source is 1:1 to 1:5. Certainly, those skilled in the art may select other suitable nitriding temperatures, bias voltages, total gas pressure, nitriding time and/or flow ratios of nitrogen to hydrogen.

Hardness of the foregoing prepared lumen stent is 250-350HV0.05/10. Compared with the lumen stent preform, a microstructure of the lumen stent remains unchanged, and still has a grain size number greater than or equal to 9 or maintains an initial cold deformed structure. Radial strength of the lumen stent is 1.1-2 times higher than that of an initial stent; an in-vitro corrosion speed is 0.25-1.5 times higher than that of the lumen stent preform; over plasticity is at least 20%, generally 30-50%, thus satisfying the requirement that over plasticity of a conventional lumen stent is at least 20%. For a coronary stent whose wall thickness is within a range of 40-150 μm, metal coverage is 11-16%, and an OD is 2-5.0 mm, radial strength thereof is at least 80 kPa, generally 80-260 kPa, thus satisfying the requirement that radial strength of the coronary stent is at least 80 kPa. For a peripheral stent whose wall thickness is within a range of 90-200 μm, metal coverage is 7-11%, and an OD is 5.0-14 mm, radial strength thereof is at least 50 kPa, generally 85-130 kPa, thus satisfying the requirement that radial strength of a conventional peripheral stent is at least 50 kPa. In conclusion, the lumen stent prepared by performing plasma nitriding on a lumen stent preform provided by the present invention satisfies mechanical properties of a conventional lumen stent. It should be known that parameters listed herein are only used for illustration, and are not intended to limit the present invention. Any lumen stent preform and lumen stent obtained based on the teachings of the present invention and the preparation methods used by them all fall within the scope of the present invention.

Figures 2A, 2B:
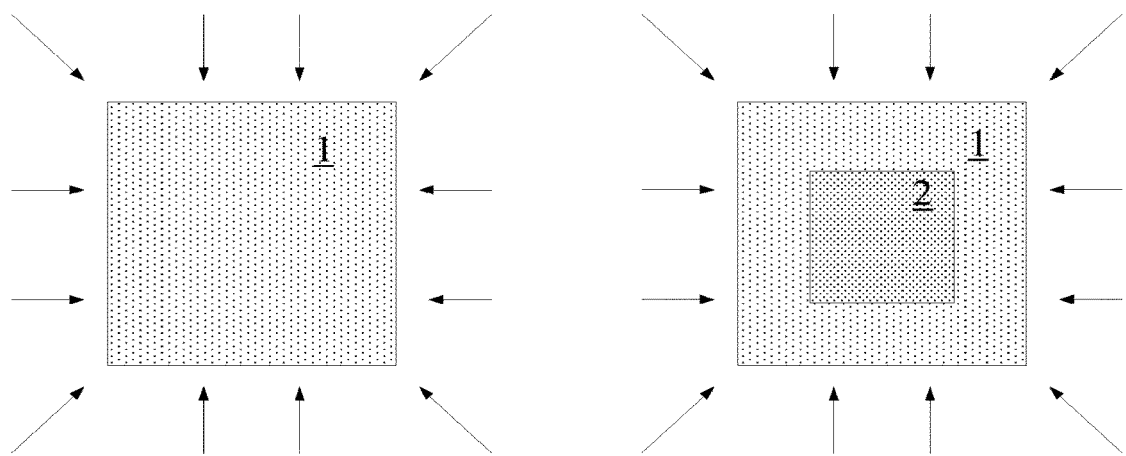
FIGS. 2a-2c are schematic diagrams of a constituent structure of a lumen stent according to an embodiment of the present invention.
Figure 2C:
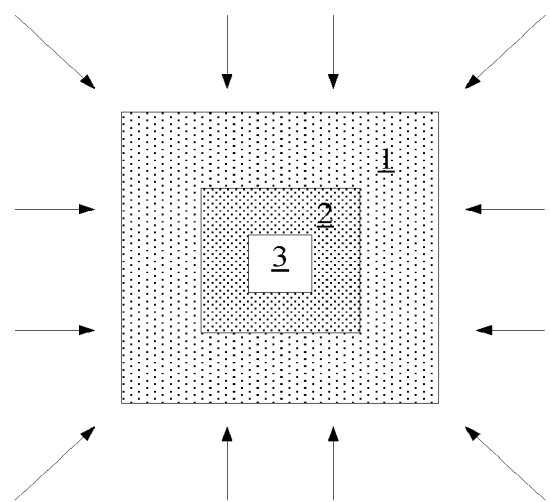

An internal structure of the lumen stent provided in the present invention may be adjusted according to actual preset use requirements, and specifically, a nitriding depth can be controlled by controlling a nitriding time, a nitriding temperature, and the like, so as to prepare lumen stents with different internal structures. For example, FIGS. 2a-2c are schematic diagrams of an internal constituent structure of a lumen stent. A square in the FIGS. illustrates a cross-section of a particular component of the lumen stent, and the square is only illustrative, and certainly a circle or another cutting shape is also possible. An arrowhead in the FIGS. illustrates a plasma nitriding direction, that is, permeating uniformly inwards from various places on a surface. Referring to FIG. 2a, the internal constituent structure of the lumen stent is a single uniform structure 1. The structure 1 includes a solid solution and an iron-nitrogen compound. The iron-nitrogen compound is diffused in the solid solution. The solid solution is a nitrogenous iron solid solution. The iron-nitrogen compound includes, but is not limited to, Fe4N and Fe2-3N. Alternatively, when the lumen stent preform is an iron alloy containing a strong nitride-forming element, the foregoing single uniform structure 1 includes a solid solution, an iron-nitrogen compound, and a compound of a strong nitride-forming element and nitrogen. The iron-nitrogen compound and the compound of a strong nitride-forming element and nitrogen are diffused in the solid solution. The iron-nitrogen compound includes, but is not limited to, Fe4N and Fe2-3N.

Referring to FIG. 2b, from a surface of the lumen stent inwards, that is, along the permeation direction shown by the arrowhead, the internal constituent structure of the lumen stent sequentially includes a first laminated structure 1 and a second laminated structure 2. The first laminated structure 1 includes a solid solution and an iron-nitrogen compound. The iron-nitrogen compound is diffused in the solid solution. The second laminated structure 2 includes a solid solution layer. The solid solution is a nitrogenous iron solid solution. Alternatively, when the lumen stent preform is an iron alloy containing a strong nitride-forming element, the difference lies in that the first laminated structure 1 includes a solid solution, an iron-nitrogen compound, and a compound of a strong nitride-forming element and nitrogen. The iron-nitrogen compound and the compound of a strong nitride-forming element and nitrogen are diffused in the solid solution.

Referring to FIG. 2c, from a surface of the lumen stent inwards, that is, along the permeation direction shown by the arrowhead, the internal constituent structure of the lumen stem sequentially includes a first laminated structure 1, a second laminated structure 2, and a third laminated structure 3. The first laminated structure 1 includes a solid solution and an iron-nitrogen compound. The iron-nitrogen compound is diffused in the solid solution. The second laminated structure 2 includes a solid solution; and the third laminated structure 3 is an iron core layer; the solid solution is a nitrogenous iron solid solution, and the material in the iron core layer 3 is an original iron-based material. Alternatively, when the lumen stent preform is an iron alloy containing a strong nitride-forming element, the difference lies in that the first laminated structure 1 includes a solid solution, an iron-nitrogen compound, and a compound of a strong nitride-forming element and nitrogen. The iron-nitrogen compound and the compound of a strong nitride-forming element and nitrogen are diffused in the solid solution.

It should be known that the laminated constituent structures in FIGS. 2b and 2c are only illustrative structures. In practice, with permeation of nitrogen ions, one constituent structure gradually becomes another adjacent constituent structure, for example, a solid solution layer 2 in FIG. 2c gradually becomes the iron core layer 3. However, when nitriding process parameters are changed or a lumen stent with a smaller wall thickness is selected, plasma nitriding further deepens, one side, close to the solid solution layer 2, of the iron core layer 3 gradually forms a solid solution; when the entire iron core layer 3 forms the solid solution, the constituent structure in FIG. 2b is formed in FIG. 2c. Further, for the constituent structure in FIG. 2b, with continued deepening of plasma nitriding, more and more iron-nitrogen compounds are formed in the solid solution layer 2; when uniform iron-nitrogen compounds are diffused in the entire solid solution layer 2, the constituent structure in FIG. 2a is formed, that is, the internal constituent structure of the lumen stein is a single structure, the entirety is the solid solution, and the iron-nitrogen compounds are diffused in the solid solution.

In addition, a compound layer may further be possibly formed on an outermost surface of the lumen stent, where the compound layer is also referred to as a white bright layer (not shown in the FIGS.); all components of the white bright layer are iron-nitrogen compounds, and a polishing process mentioned in step 103 or any other suitable manner may be used to remove the white bright layer to obtain the final lumen stent.

Based on the above, it can be seen that not only surface alloying modification treatment is adapted to be performed on the lumen stent preform provided in the present invention by means of plasma nitriding, but also plasma nitriding may be implemented in a relatively large temperature range (320-560° C.), so that the plasma nitriding process is applicable to preparation of a lumen stent on a large scale for commercial purposes.

Reversion may usually occur in pure iron or iron alloys at about 400° C., and the pure iron or iron alloys begin to recrystallize to anneal at about 500° C. When plasma nitriding is performed at a high temperature, for example, higher than 500° C., reversion and recrystallization annealing may occur in the pure iron or iron alloys. Reversion means that when a heat treatment temperature is not high, defects such as grain internal vacancies and interstitial atoms are greatly reduced by means of movement and compounding, but because of low diffusion capabilities of atoms, dislocations introduced by cold deformation still remain and microstructures of deformed metals do not obviously change. Reversion improves plasticity of materials, and slightly reduces strength and hardness thereof. Recrystallization means a process in which new grains without strains are generated when an annealing temperature is high enough and time is long enough in a microstructure of a deformed metal or alloy on which cold machining is performed, the new grains grow up constantly until the original deformed structure on which cold machining is performed completely disappears, and performance of the metal or alloy also Prominently changes. Recrystallization prominently improves plasticity of materials, and prominently reduces strength and hardness of the materials at the same time.

It can be seen that a nitriding temperature has a great effect on material attributes of a lumen stent. If a temperature below 400° C. is selected to perform nitriding to avoid effects brought by reversion and/or recrystallization, nitrogen ions that permeate can hardly overcome a diffusion energy barrier, and cannot effectively diffuse within the material, therefore, nitriding effects are reduced. That is, both the nitriding effects and avoidance of effects brought by reversion and/or recrystallization cannot be ensured only by lowering the nitriding temperature. The present invention further provides a lumen preform. Not only low-temperature nitriding is adapted to be performed on the lumen preform to avoid effects brought by reversion and/or recrystallization as much as possible, but also effective diffusion of nitrogen ions within the material can be ensured in the nitriding process.

In an embodiment of the present invention, the hardness of the lumen stent preform manufactured in step 101 is 200-250HV0.05/10, and the microstructure is a deformed structure after cold machining. The lumen stent preform is made into an initial stent and plasma nitriding is performed thereon. Plasma nitriding for 30-180 min may be performed on the foregoing 320-420° C. initial stent under conditions of a bias voltage of 500-700V, total air pressure of 50-500 pa, and a nitrogen to hydrogen ratio of 1:1-1:3, so as to prepare a lumen stent with hardness of 300-350HV0.05/10 and a microstructure that still maintains the deformed structure after cold machining. Radial strength of the lumen stent is 1.1-2 times higher than that of the initial stent; an in-vitro corrosion speed is 1-1.5 times higher than that of the lumen stent preform, and the over-plasticity is at least 20%, and generally may reach 30-40%. For a coronary stent whose wall thickness is within a range of 40-150 μm, metal coverage is 11-16%, and OD is 2-5.0 mm, radial strength thereof is at least 80 kPa, generally 110-260 kPa, it could satisfy the requirement that radial strength of the conventional coronary stent is at least 80 kPa. For a peripheral stent whose wall thickness is 90-200 μm, metal coverage is 7-11%, and OD is 6-14 mm, radial strength thereof is at least 50 kPa, generally 85 kPa, even higher, 130 Kpa, it could satisfy the requirement that radial strength of the conventional peripheral stent is at least 50 kPa. In conclusion, the lumen stent prepared in the present embodiment satisfies the mechanical property requirements of a conventional lumen stent. It should be known that parameters listed herein are only used for illustration, and parameters of lumen stents with different specifications are not completely the same, and therefore the parameters are not intended to limit the present invention. Any lumen stent preform and lumen stent obtained based on the teachings of the present invention and the preparation methods used by them all fall within the scope of the present invention.

In the present embodiment, the microstructure of the lumen stent preform includes a cold deformed structure with a large quantity of vacancy defects, broken grain boundaries, and energy of cold deformation being stored inside the material thereof, so that nitrogen atoms first permeate into the grain boundaries and then diffuse inside the grains; and deformed structures and fine grain materials have more grain boundaries with respect to equiaxed grains and provide more channels for permeation of nitrogen atoms. In addition, material deformation stored energy introduced by cold machining can help nitrogen atoms overcome a diffusion energy barrier, and the nitrogen atoms can diffuse inside the material even at a low nitriding temperature. Low-temperature plasma nitriding can be performed under a condition of 320-420° C. by using the lumen stent preform. Improvement of the material strength and hardness and corrosion rate brought by vacancies and dislocations after cold machining are stored, combined with the improvement of the strength and hardness and corrosion rate brought by plasma nitriding, which makes the hardness, in-vitro corrosion rate and plasticity of the lumen stent all satisfy the requirements. That is, using the lumen stent preform can overcome effects of excessively high temperatures on plasticity and strength of the lumen stent in the high temperature plasma nitriding process.

On the aspect of performance test of the lumen stent, radial strength of the lumen stent can uniformly apply radial pressure to the stent by means of a compression module, to make the stem compressed and generate uniform deformation. It is defined that the radial pressure applied to the stent when the stent radially (the outer diameter) generates 10% deformation is the radial strength of the stent. For example, a hollowed initial stent can be made by selecting a pure iron tube through laser engraving according to a preset decorative pattern design, where a nominal diameter of the stent is 3.0 mm and a length of the stent is 18 mm. Then coarse polishing is performed on the stent, and the stent is placed into a plasma vacuum nitriding furnace to undergo nitriding, and then fine polishing is performed on the stent to obtain a preset size of a finished product. When the finished product of the stent is expanded in a balloon manner to the nominal diameter 3.0 mm, a radial strength test and a corrosion rate during in-vitro soaking test are performed.

A plasticity test of the lumen stent is performed according to the following example. By using a stent with a specification of an OD of 3.0×18 mm (OD is 3.0 mm; a tube length is 18 mm) as an example, when an assorted 3.0×18 mm balloon catheter is used to expand to the pressure of a nominal diameter of the balloon catheter (there is usually an annotation on the balloon catheter, generally 8 atm), an inner diameter of the stent is 3.0 mm, which is the nominal diameter of the stent. When stents with the same specification made of preforms of different materials are gradually expanded from small to large by using balloon catheters with different nominal diameters or different expansion pressure, fractures of the stents are observed, and maximum expansion diameters D (mm) of the stents when the stents are expanded and do not crack are recorded, 100×(D−3.0)/D % is calculated to characterize over-plasticity of the material. A larger maximum expansion diameter of the stent when the stent is expanded and does not crack indicates better anti-fracture performance and higher plasticity of the stent. If the stem cracks before being expanded to 1.2 times of the nominal diameter (equivalent to 20% over-plasticity), the material has excessively low plasticity in the existing drawing process or after corresponding modification treatment in the existing drawing process, and cannot be used to prepare a stent.

An in-vitro soaking corrosion test of a lumen stent is as follows: a stent after polishing treatment is expanded to a nominal diameter by using a balloon catheter, and is weighed initially by a balance with a millionth precision, and the weight is recorded as MO, accurate to 0.001 mg. A soaking corrosion medium is a 0.9% NaCl saline solution; a proportion of a surface area of the sample to a volume of the soaking corrosion medium is 0.05 cm2/ml (equivalent to that a 3.0×18 mm stent with a wall thickness of 50 µm and a rod width of 90 µm is soaked in a 15 ml medium described in the embodiment), and the sample is placed in a 37° C. shaking bath in an open manner for soaking and corrosion for 2 h. The stent after corrosion is ultra-cleaned for 3-5 min by using a 3-5% tartaric acid solution until corrosion products are completely removed, and then is placed in a 2% sodium hydroxide aqueous solution for neutralization for 10 min, is cleaned by using deionized water for 5 min, and finally is dehydrated for 10 min by using absolute ethyl alcohol. After ethyl alcohol is completely volatilized, the stent is weighed by using the balance with millionth precision, and the weight is recorded as Ml, accurate to 0.001 mg. Assuming that corrosion proceeds at a constant speed as time passes, then a weightlessness result of the in-vitro soaking corrosion is represented as mm/y, and a calculation formula is (10·2·ΔM)/(p·S·t), ΔM is calculated by an input of a number with a unit of mg, t is calculated by an input of a number with a unit of year y, S is calculated by an input of a number with a unit of cm2, and p is calculated by an input of a number with a unit of g/cm2, for example, the material is pure iron, and p=7.8 g/cm2).

Embodiment 1

Figure 2:
FIG. 2 is a cross-sectional metallographic diagram of a pure iron tubular product having hardness of 160HV0.05/10 and an OD of 1.6 mm.
Figure 3:
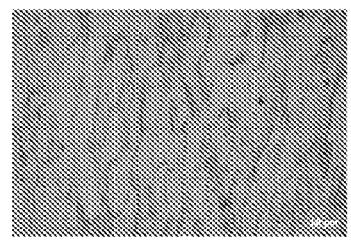
FIG. 3 is a longitudinal-sectional metallographic diagram of the pure iron tubular product in FIG. 2.
Figure 4:
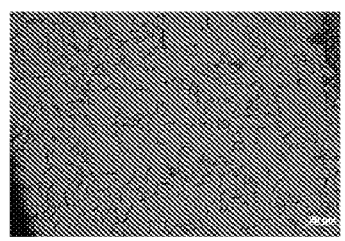
FIG. 4 is a cross-sectional metallographic diagram of a pure iron tubular product having hardness of 160HV0.05/10 and an OD of 4.2 mm.
Figure 5:
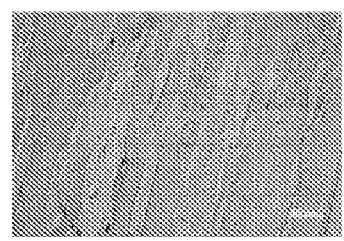
FIG. 5 is a longitudinal-sectional metallographic diagram of the pure iron tubular product in FIG. 4.

This embodiment provides a method for preparing a lumen stent by using a pure iron tubular product. The lumen stent preform prepared by drawing the blank in step 101 has an ultra-thin wall. From the metallographic diagrams of FIGS. 2-5, it can be obviously seen that grains of the pure iron tube are refined, and are not equiaxed grains any more. FIG. 2 and FIG. 3 respectively show a cross-sectional metallographic phase and a longitudinal-sectional metallographic phase of a pure iron tubular product with hardness of 160HV0.05/10 and an OD of 1.6 mm after drawing. FIG. 4 and FIG. 5 respectively show a cross-sectional metallographic phase and a longitudinal-sectional metallographic phase of a pure iron tubular product with hardness of 160HV0.05/10 and an OD of 4.2 mm after drawing. According to the FIGS., it can be known that grains are elongated along a drawing direction of a tubular blank.

A drawing process with a long mandrel may be used to prepare a tubular product with high precision by means of drawing, and drawing passes that need to be used depend on the hardness and plasticity of a blank. In this embodiment, a 6×0.5 (with an outer diameter of 6 mm and a wall thickness of 0.5 mm) pure iron tubular blank having a completely annealed structure is used (a total impurity element content is less than or equal to 0.5 wt. %, where a carbon content is less than or equal to 0.022%). The pure iron tubular blank has a hardness of about 90HV0.05/10, and the metallurgical structure of the completely annealed structure is equiaxed grain with a grain size number greater than or equal to 4.

The used drawing passes sequentially include: (1) Drawing with a long mandrel by means of a 5 mm external mold and a 4.4 mm mandrel; (2) Drawing with a long mandrel by means of a 4.4 mm external mold and a 4.0 mm mandrel, where an annealing pass may be supplemented after completion of this drawing pass, for example, annealing may be performed for half an hour at 650° C. after completion of this drawing pass; (3) Drawing with a long mandrel by means of a 3.5 mm external mold and a 3.19 mm mandrel; (4) Drawing with a long mandrel by means of a 2.3 mm external mold and a 2.02 mm mandrel; (5) Drawing with a long mandrel by means of a 1.83 mm external mold and a 1.60 mm mandrel, where an annealing pass may be supplemented after completion of this drawing pass, for example, annealing may be performed for half an hour at 510° C. after completion of this drawing pass; and (6) Drawing without a mandrel by means of a 1.62 mm external mold, to obtain a stent preform with a microstructure whose state is close to a completely annealed state, and the drawing without a mandrel is the last pass during this drawing.

In order to reduce the generation of drawing defects, drawing coefficients (or may be referred to as elongation coefficients) of all the drawing passes should not exceed 2.0, and the elongation coefficients in the embodiment may be selected as about 1.5. Because metal materials have a certain elastic aftereffect, for example, the outer diameter will rebound somewhat after drawing with the 1.62 mm external mold, the outer diameter is measured to be 1.63 mm and the wall thickness is measured to be 0.125 mm. In order to strictly control the quality of the external surface of the tubular product, an allowance of 0.03 mm is reserved for polishing. After mechanical polishing of 0.03 mm, a finished product pure iron tube with the same ingredients (a total impurity element content is less than or equal to 0.5 wt. %, where a carbon content is less than or equal to 0.022%), an outer diameter of 1.60 mm, a wall thickness of 0.110±0.005 mm, hardness of about 160HV0.05/10, and a grain size number of 9 or above, is obtained as a lumen stent preform. Quality of an internal wall of the tubular product is obtained by controlling the mandrel. A surface of the mandrel needs to be fine-polished, and no obvious mechanical processing traces are observed under a 200× stereomicroscope, and the hardness reaches HRC58-64; the material of the mandrel may be die block steel such as SKD11 or SKH-9. Size uniformity of the tubular product is obtained by strictly controlling the precision sizes of the mandrel and the external mold, and precision of the external mold is less than or equal to ±3 μm, and precision of the mandrel is less than or equal to ±2 μm.

In step 102, the foregoing lumen stent preform is cut with laser, at a cutting accuracy of ±5 μm, to obtain a coronary initial stent with a specification of 3.0×18 mm. When the stent is expanded to 3.0 mm in diameter, the metal mesh coverage on the surface is about 13%. The laser-cut pure iron stent is polished to a finished size (with a rod width of 90 μm and a wall thickness of 70 μm), and measured to have radial strength of about 80 kPa, a corrosion rate during in-vitro soaking of about 1.0 mm/y, and over-plasticity of about 50%.

In step 103, after rough polishing and cleaning, the laser-cut pure iron stent is placed into a glow plasma furnace for plasma nitriding treatment. A nitriding temperature of about 560° C., a flow ratio of nitrogen to hydrogen of 1:3, air pressure of 50-130 Pa, and a bias voltage of 500V are selected to perform the nitriding for 90-150 min. The entire cross-section of the stent rod is permeated, that is, except the compound layer on the outermost surface, the constituent structure is shown in FIG. 2a. The nitrided iron stent is embedded with a resin, and is ground and polished. Results of metallographic observation and hardness test show that the microstructure remains unchanged, that is, the grain size number is greater than or equal to 9, and the hardness value is improved to about 250HV0.05/10. Another nitrided iron stent sample is taken and polished to a finished size with a rod width of 90 μm and a wall thickness of 70 μm, and measured to have radial strength of the thin-wall stent improved to 115 kPa, over-plasticity of 50%, and a corrosion rate during in-vitro soaking improved to 1.5 mm/y.

Embodiment 2

In step 101, a 6×0.5 (with an outer diameter of 6 mm and a wall thickness of 0.5 mm) pure iron tubular blank having a completely annealed structure (a total impurity element content is less than or equal to 0.5 wt. %, where a carbon content is less than or equal to 0.022%) is drawn to prepare a lumen stent preform. The pure iron tubular blank has a hardness of about 90HV0.05/10, and the metallurgical structure of the completely annealed structure is equiaxed grain with a grain size number greater than or equal to 4. Drawing passes include: (1) Drawing with a long mandrel by means of a 5 mm external mold and a 4.4 mm mandrel; (2) Drawing with a long mandrel by means of a 4.4 mm external mold and a 4.0 mm mandrel; (3) Drawing with a long mandrel by means of a 3.5 mm external mold and a 3.19 mm mandrel, where an annealing pass may be supplemented after this drawing pass, for example, annealing may be performed for half an hour at 500° C. after completion of this drawing pass; (4) Drawing with a long mandrel by means of a 2.3 mm external mold and a 2.02 mm mandrel; (5) Drawing with a long mandrel by means of a 1.78 mm external mold and a 1.60 mm mandrel, where an annealing pass may be supplemented after this drawing pass, for example, annealing may be performed for half an hour at 400° C. after completion of this drawing pass; and (6) Drawing without a mandrel by means of a 1.62 mm external mold, and the drawing without a mandrel is the last pass during this drawing.

Figure 6:
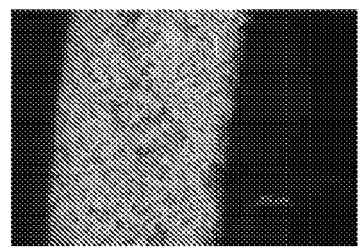
FIG. 6 is a cross-sectional metallographic diagram of a lumen stent preform having an OD of 1.6 mm and having a cold-deformed structure.
Figure 7:
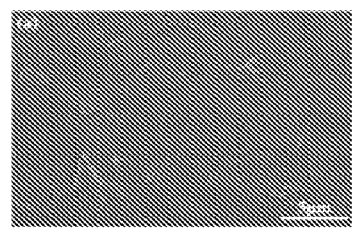
FIG. 7 is a cross-sectional morphologic diagram of a lumen stent preform having an OD of 1.6 mm and having a cold-deformed structure under a scanning electron microscope.
Figure 8:
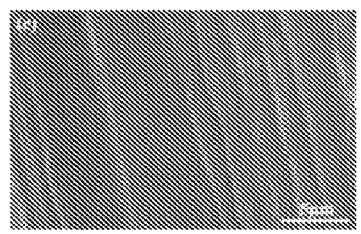
FIG. 8 is a longitudinal-sectional morphologic diagram of a lumen stent preform having an OD of 1.6 mm and having a cold-deformed structure under a scanning electron microscope.

In order to reduce generation of drawing defects, elongation coefficients of all the drawing passes should not exceed 2.0, and a range of the elongation coefficients (drawing coefficients) is 1.2-2.0, and the elongation coefficients may be selected as about 1.5. Because metal materials have a certain elastic aftereffect, the outer diameter will rebound somewhat after drawing with the 1.62 mm external mold, and the outer diameter is measured to be 1.63 mm and the wall thickness is measured to be 0.095 mm. In order to strictly control quality of the external surface of a tubular product, an allowance of 0.03 mm is reserved for polishing. After mechanical polishing of 0.03 mm, a finished product pure iron tube with the same ingredients (a total impurity element content is less than or equal to 0.5 wt. %, and a carbon content is less than 0.022%), an outer diameter of 1.60 mm, a wall thickness of 0.080±0.005 mm, hardness of about 200HV0.05/10, and a deformed structure after cold machining, is obtained as a stent preform. FIG. 6 is a cross-sectional metallographic diagram of the foregoing lumen stent preform having an OD of 1.6 mm and having a cold-deformed structure. FIG. 7 is a cross-sectional morphologic diagram of the foregoing lumen stent preform having an OD of 1.6 mm and having a cold-deformed structure under a scanning electron microscope. FIG. 8 shows longitudinal-sectional morphology of the foregoing lumen stent preform having an OD of 1.6 mm and having a cold-deformed structure under a scanning electron microscope.

In step 102, the foregoing prepared lumen stent preform is cut with laser, at a cutting accuracy of ±5 μm, to obtain a coronary initial stent with a specification of OD 3.0×18 mm. When the stent is expanded to 3.0 mm in diameter, the metal mesh coverage on the surface is about 13%. The laser-cut initial stent is polished to a finished size (with a rod width of 90 μm and a wall thickness of 50 μm), and measured to have radial strength of 80 kPa, a corrosion rate during in-vitro soaking of 1.0 mm/y, and over-plasticity of 50%.

In step 103, after rough polishing and cleaning, the laser-cut initial stent is placed into a glow plasma furnace for nitriding treatment. A nitriding temperature of 480° C., a flow ratio of nitrogen to hydrogen of 1:1, air pressure of 10-20 Pa, and a bias voltage of about 600V are selected to perform the nitriding for 60-120 min. The cross-section of the stent rod is permeated, that is, except the compound layer on the outermost surface, the constituent structure is shown in FIG. 2a. The nitrided iron stent is embedded with a resin, and is ground and polished. Results of metallographic observation and hardness test show that the material still maintains a deformed structure, and the hardness value is improved to about 2501-HV0.05/10. Another nitrided iron stent sample is taken and polished to a finished size (with a rod width of 90 μm and a wall thickness of 50 μm), and measured to have radial strength of the stent improved to about 90 kPa, over-plasticity remains of 50%, and a corrosion rate during in-vitro soaking improved to 1.75 mm/y.

Embodiment 3

In step 101, a pure iron blank is drawn to obtain a lumen stent preform. The pure iron blank is a 6×0.5 (with an outer diameter of 6 mm and a wall thickness of 0.5 mm) pure iron tubular blank having a completely annealed structure (a total impurity element content is less than or equal to 0.5 wt. %, where a carbon content is less than or equal to 0.022%). The pure iron tubular blank has a hardness of about 90HV0.05/10, and the metallurgical structure of the completely annealed structure is equiaxed grain with a grain size number greater than or equal to 4. Drawing passes include: (1) Drawing with a long mandrel by means of a 5 mm external mold and a 4.4 mm mandrel; (2) Drawing with a long mandrel by means of a 4.4 mm external mold and a 4.0 mm mandrel; (3) Drawing with a long mandrel by means of a 3.5 mm external mold and a 3.19 mm mandrel; (4) Drawing with a long mandrel by means of a 2.3 mm external mold and a 2.02 mm mandrel; (5) Drawing with a long mandrel by means of a 1.8 mm external mold and a 1.63 mm mandrel; and (6) Drawing without a mandrel by means of a 1.62 mm external mold, and the drawing without a mandrel is the last pass during this drawing.

In order to reduce the generation of drawing defects, elongation coefficients of all the drawing passes should not exceed 2.0, and the elongation coefficients may be selected as about 1.5. Because metal materials have a certain elastic aftereffect, the outer diameter will rebound somewhat after drawing with the 1.62 mm external mold, and the outer diameter is measured to be 1.63 mm and the wall thickness is measured to be 0.095 mm. In order to strictly control the quality of the external surface of a tubular product, an allowance of 0.03 mm is reserved for polishing. After mechanical polishing of 0.03 mm, a finished product pure iron tube with the same ingredients (a total impurity element content is less than or equal to 0.5 wt. %, where a carbon content is less than or equal to 0.022%), an outer diameter of 1.60 mm, a wall thickness of 0.080±0.005 mm, hardness of about 250HV0.05/10, and a deformed structure after cold machining, is obtained as a stent preform.

In step 102, the foregoing prepared lumen stent preform is cut with laser, at a cutting accuracy of ±5 μm, to obtain a coronary initial stent with a specification of OD 3.0×18 mm. When the stent is expanded to 3.0 mm in diameter, the metal mesh coverage on the surface is about 13%. The laser-cut initial stent is polished to a finished size (with a rod width of 90 μm and a wall thickness of 50 μm), and measured to have radial strength of 90 kPa, a corrosion rate during in-vitro soaking of 1.0 mm/y, and over-plasticity of 40%.

In step 103, after rough polishing and cleaning, the laser-cut initial stent is placed into a glow plasma furnace for nitriding treatment. A nitriding temperature of about 320° C., a flow ratio of nitrogen to hydrogen of 1:3, air pressure of 380-500 Pa, and a bias voltage of about 700V are selected to perform the nitriding for 90-150 min. The cross-section of the stent rod is permeated, that is, except the compound layer on the outermost surface, an interior structure of the material is shown in FIG. 2a. The nitrided lumen stent is embedded with a resin, and is ground and polished. Results of metallographic observation and hardness test show that the material still maintains a deformed structure, and the hardness is improved to 300HV0.05/10. Another nitrided iron stent sample is taken and polished to a finished size (with a rod width of 90 μm and a wall thickness of 50 μm), and measured to have radial strength of the stent improved to 110 kPa, over-plasticity reaching 35%, and a corrosion rate during in-vitro soaking improved to 2.0 mm/y.

Embodiment 4

In step 101, an iron alloy blank is drawn to obtain a lumen stent preform. The iron alloy blank is a 6×0.5 (with an outer diameter of 6 mm and a wall thickness of 0.5 mm) iron alloy blank having a completely annealed structure, and an alloy element of the iron alloy contains no strong nitride-forming element, for example, Ti, Cr, Al, Zr, Nb, V, B, W, or Mo. C content is 0.3 wt. %, Si content is 0.30 wt. %, Mn content is 0.60 wt. %, P content is 0.025 wt. %, S content is 0.025 wt. %, Ni content is 0.25 wt. %, and Cu content is 0.25 wt. %, that is, a total alloy element content of the iron alloy is 1.75 wt. %. The iron alloy tubular blank has a hardness of 130HV0.05/10. Further, different hardness can be obtained by changing ingredients of the alloy, for example, a hardness range of 100-150HV0.05/10 may also be selected. The completely annealed metallurgical structure is equiaxed grain with a grain size number greater than or equal to 4.

Drawing passes include: (1) Drawing with a long mandrel by means of a 5 mm external mold and a 4.4 mm mandrel; (2) Drawing with a long mandrel by means of a 4.4 mm external mold and a 4.0 mm mandrel; (3) Drawing with a long mandrel by means of a 3.5 mm external mold and a 3.19 mm mandrel, where an annealing pass may be supplemented after completion of this drawing pass, for example, annealing may be performed for half an hour at 550° C. after completion of this drawing pass; (4) Drawing with a long mandrel by means of a 2.3 mm external mold and a 2.02 mm mandrel; (5) Drawing with a long mandrel by means of a 1.83 mm external mold and a 1.60 mm mandrel, where an annealing pass may be supplemented after completion of this drawing pass, for example, annealing may be performed for half an hour at 430° C. after completion of this drawing pass; and (6) Drawing without a mandrel by means of a 1.62 mm external mold, and the drawing without a mandrel is the last pass during this drawing.

In order to reduce the generation of drawing defects, elongation coefficients of all the drawing passes should not exceed 2.0, and the elongation coefficients may be selected as about 1.5. Because metal materials have a certain elastic aftereffect, the outer diameter will rebound somewhat after drawing with the 1.62 mm external mold, and the outer diameter is measured to be 1.63 mm and the wall thickness is measured to be 0.125±0.005 mm. In order to strictly control quality of the external surface of a tubular product, an allowance of 0.03 mm is reserved for polishing. After mechanical polishing of 0.03 mm, an iron alloy stent preform with the same material as the blank, an outer diameter of 1.6 mm, a wall thickness of 0.110±0.005 mm, hardness of about 200HV0.05/10, and a deformed structure after cold machining, is obtained.

In step 102, the foregoing prepared lumen stent preform is cut with laser, at a cutting accuracy of ±5 μm, to obtain a coronary initial stent with a specification of OD 3.0×18 mm. When the stent is expanded to 3.0 mm in diameter, the metal mesh coverage on the surface is about 13%. The laser-cut iron alloy initial stent is polished to a finished size (with a rod width of 90 μm and a wall thickness of 70 μm), and measured to have radial strength of 92 kPa, a corrosion rate during in-vitro soaking of 1.0 mm/y, and over-plasticity of 50%.

In step 103, after rough polishing and cleaning, the laser-cut initial stent is placed into a glow plasma furnace for nitriding treatment. A nitriding temperature of 380° C., a flow ratio of nitrogen to hydrogen of 1:3, air pressure of 50-130 Pa, and a bias voltage of about 650V are selected to perform the nitriding for 60-120 min. The cross-section of the stent rod is permeated, that is, except the compound layer on the outermost surface, a single diffusion layer penetrates through a wall thickness direction of the entire stent rod. The nitrided iron alloy stent after nitriding treatment is embedded with a resin, and is ground and polished. Results of metallographic observation and hardness test show that the material still maintains a deformed structure, and the hardness value is improved to 350HV0.05/10. Another nitrided iron alloy stent sample is taken and polished to a finished size (with a rod width of 90 μm and a wall thickness of 70 μm), and measured to have radial strength of the stent prominently improved to about 180 kPa, over-plasticity reaching 40%, and a corrosion rate during in-vitro soaking improved to 2.25 mm/y.

Embodiment 5

In step 101, an iron alloy blank is drawn to obtain a lumen stent preform. The blank is a 6×0.5 (with an outer diameter of 6 mm and a wall thickness of 0.5 mm) iron alloy tubular blank having a completely annealed structure. A total alloy element content of less than or equal to 3 wt. %, where a carbon content is less than or equal to 0.45 wt. %, and the alloy element contains no strong nitride-forming element, for example, Ti, Cr, Al, Zr, Nb, V, B, NV, or Mo. The iron alloy tubular blank has a hardness of 100-150HV0.05/10. Different alloy ingredients will lead to slightly different hardness. The completely annealed metallurgical structure is equiaxed grain with a grain size number greater than or equal to 4.

Drawing passes include: (1) Drawing with a long mandrel by means of a 5 mm external mold and a 4.4 mm mandrel; (2) Drawing with a long mandrel by means of a 4.4 mm external mold and a 4 mm mandrel; (3) Drawing with a long mandrel by means of a 3.5 mm external mold and a 3.21 mm mandrel, where an annealing pass may be supplemented after this drawing pass, for example, annealing may be performed for half an hour at 530° C. after completion of this drawing; and (4) Drawing without a mandrel by means of a 3.015 mm external mold, and the drawing without a mandrel is the last pass during this drawing.

In order to reduce the generation of drawing defects, elongation coefficients of all the drawing passes should not exceed 2.0, and the elongation coefficients may be selected as about 1.5. Because metal materials have a certain elastic aftereffect, the outer diameter will rebound somewhat after drawing with the 3.015 mm external mold, and the outer diameter is measured to be 3.03 mm and the wall thickness is measured to be 0.170 mm. In order to strictly control the quality of the external surface of a tubular product, an allowance of 0.03 mm is reserved for polishing. After mechanical polishing of 0.03 mm, a finished pure iron tube with the same material as the blank, an outer diameter of 3.0 mm, a wall thickness of 0.155 mm+0.005 mm, hardness of about 160HV0.05/10, and a grain size number greater than or equal to 9, is obtained as a stent preform.

In step 102, the stent preform manufactured above is selected and cut with laser to obtain a peripheral initial stent with a specification of OD 8.0×18 mm, at a cutting accuracy of +5 μm. When the stent is expanded to 3.0 mm in diameter, the metal mesh coverage on the surface is about 13%. The laser-cut initial stent is polished to a finished size (with a rod width of the stent at 178 μm and a wall thickness of the stent at 120 μm), and measured to have radial strength of 65 kPa, a corrosion rate during in-vitro soaking of 1.0 mm/y and over-plasticity of 50%.

In step 103, after rough polishing and cleaning, the laser-cut initial stent is placed into a glow plasma furnace for nitriding treatment. A nitriding temperature of 560° C., a flow ratio of nitrogen to hydrogen of 1:3, air pressure of 50-130 Pa, and a bias voltage of about 600V are selected to perform the nitriding for 90-150 min. The cross-section of the stent rod is permeated, that is, except the compound layer on the outermost surface, the interior has a structure as shown in FIG. 2a. The nitrided iron stent after the nitriding treatment is embedded with a resin, and is ground and polished. Results of metallographic observation and hardness test show that the grain size number of the material is still greater than or equal to 9, and the hardness value is improved to about 250HV0.05/10. Another nitrided iron stent sample is taken and polished to a finished size (with a rod width of 178 μm and a wall thickness of 120 μm), and measured to have radial strength improved to 90 kPa, over-plasticity maintained at 50%, and a corrosion rate during in-vitro soaking improved to 1.5 mm/y.

Embodiment 6

In step 101, an iron alloy blank is drawn to obtain a lumen stent preform. This blank is a 6×0.5 (with an outer diameter of 6 mm and a wall thickness of 0.5 mm) iron alloy blank having a completely annealed structure, and contains no strong nitride-forming element, for example, Ti, Cr, Al, Zr, Nb, V, B, W, or Mo, and has C of 0.4 wt. %, Si of 0.4 wt. %, Mn of 0.65 wt. %, P of 0.04 wt. %, S of 0.04 wt. %, Ni of 0.5 wt. %, and Cu of 0.5 wt. %, that is, a total alloy element content is 2.53 wt. %. The iron alloy tubular blank has a hardness of 140HV0.05/10. Further, different hardness can be obtained by changing ingredients of the alloy, for example, a hardness range of 100-150HV0.05/10 may also be selected. The completely annealed metallurgical structure is equiaxed grain with a grain size number greater than or equal to 4.

Drawing passes include: (1) Drawing with a long mandrel by means of a 5 mm external mold and a 4.4 mm mandrel; (2) Drawing with a long mandrel by means of a 4.4 mm external mold and a 3.96 mm mandrel; and (3) Drawing without a mandrel by means of a 4.22 mm external mold, and the drawing without a mandrel is the last pass during this drawing.

In order to reduce generation of drawing defects, elongation coefficients of all the drawing passes should not exceed 2.0, and the elongation coefficients may be selected as about 1.5. Because metal materials have a certain elastic aftereffect, for example, the outer diameter will rebound somewhat after drawing with the 4.22 mm external mold, and the outer diameter is measured to be 4.23 mm and the wall thickness is measured to be 0.235 mm. In order to strictly control quality of the external surface of a tubular product, an allowance of 0.03 mm is reserved for polishing. After mechanical polishing of 0.03 mm, a finished iron alloy tube with an unchanged material as the blank, an outer diameter of 4.2 mm, a wall thickness of 0.220±0.005 mm, hardness of about 250HV0.05/10, and a deformed structure after cold machining, is obtained as a stent preform.

In Step 102, the stent preform manufactured above is cut with laser, at a cutting accuracy of ±5 μm, to obtain a peripheral initial stent with a specification of OD 12.0×18 mm. When the stent is expanded to 3.0 mm in diameter, the metal mesh coverage on the surface is about 13%. The laser-cut iron alloy initial stent is polished to a finished size (with a rod width of 228 μm and a wall thickness of 160 μm), and measured to have radial strength of 60 kPa, a corrosion rate during in-vitro soaking of 1.0 mm/y, and over-plasticity of 35%.

In Step 103, after rough polishing and cleaning, the laser-cut initial stent is placed into a glow plasma furnace for nitriding treatment. A nitriding temperature of about 420° C., a flow ratio of nitrogen to hydrogen of 1:3, air pressure of 200-300 Pa, and a bias voltage of about 600V are selected to perform the nitriding for 120-180 min. The cross-section of the stent rod is permeated, that is, except the compound layer on the outermost surface, the interior has a structure as shown in FIG. 2a. The nitrided iron alloy stent after the nitriding treatment is embedded with a resin, and is ground and polished. Results of metallographic observation and hardness test show that the material still remains a deformed structure, and the hardness value is improved to 350HV0.05/10. Another nitrided iron alloy stent sample is taken and polished to a finished size (with a rod width of 228 μm and a wall thickness of 160 μm), and measured to have radial strength significantly improved to 85 kPa, over-plasticity still up to 30%, and a corrosion rate during in-vitro soaking significantly improved to 2.5 mm/y.

Embodiment 7

In Step 101, an iron alloy blank is drawn to obtain a lumen stent preform. A 6×0.5 (with an outer diameter of 6 mm and a wall thickness of 0.5 mm) iron alloy tubular blank having a completely annealed structure is employed, which has ingredients as follows, based on percentage by weight: C 0.10 wt. %, Si 0.17 wt. %, Mn 0.50 wt. %, P 0.03 wt. %, S 0.020 wt. %, Mo 0.45 wt. %, Cr 1.0 wt. %, Cu 0.15 wt. %, and Ni 0.25 wt. %, that is, a total alloy element content is 2.67 wt. %, and a content of the strong nitride-forming elements (Mo and Cr) is 1.45 wt. %. The iron alloy tubular blank has a hardness of 120HV0.05/10. Further, different hardness can be obtained by changing the alloy ingredients (including the strong nitride-forming element), for example, a hardness range of 100-150HV0.05/10 may also be selected. The completely annealed metallurgical structure is equiaxed grain with a grain size number greater than or equal to 4.

Drawing passes include: (1) Drawing with a long mandrel by means of a 5 mm external mold and a 4.4 mm mandrel; (2) Drawing with a long mandrel by means of a 4.4 mm external mold and a 4.0 mm mandrel, where an annealing pass may be supplemented after this drawing pass, for example, annealing may be performed for one hour at 600° C. after completion of this drawing; (3) Drawing with a long mandrel by means of a 3.5 mm external mold and a 3.19 mm mandrel; (4) Drawing with a long mandrel by means of a 2.3 mm external mold and a 2.02 mm mandrel; (5) Drawing with a long mandrel by means of a 1.83 mm external mold and a 1.60 mm mandrel, where an annealing pass may be supplemented after this drawing pass, for example, annealing may be performed for half an hour at 500° C. after completion of this drawing; and (6) Drawing without a mandrel by means of a 1.62 mm external mold, and the drawing without a mandrel is the last pass during this drawing.

In order to reduce the generation of drawing defects, elongation coefficients of all the drawing passes should not exceed 2.0, and the elongation coefficients may be selected as about 1.5. Because metal materials have a certain elastic aftereffect, the outer diameter will rebound somewhat after drawing with the 1.62 mm external mold, and the outer diameter is measured to be 1.63 mm and the wall thickness is measured to be 0.095 mm. In order to strictly control quality of the external surface of a tubular product, an allowance of 0.03 mm is reserved for polishing. After mechanical polishing of 0.03 mm, a finished iron alloy tube with the same material as the blank, an outer diameter of 1.6 mm, a wall thickness of 0.080±0.005 mm, hardness of about 230HV0.05/10, and a deformed structure after cold machining, is obtained as a stent preform.

In Step 102, the stent preform manufactured above is cut with laser, at a cutting accuracy of ±5 μm, to obtain a coronary initial stent with a specification of OD 3.0×18 mm. When the stent is expanded to 3.0 mm in diameter, the metal mesh coverage on the surface is about 13%. The laser-cut iron alloy initial stent is polished to a finished size (with a rod width of 90 μm and a wall thickness of 50 μm), and measured to have radial strength of 70 kPa, a corrosion rate during in-vitro soaking of 1.0 mm/y, and over-plasticity of 50%.

In Step 103, after rough polishing and cleaning, the laser-cut initial stent is placed into a glow plasma furnace for nitriding treatment. A nitriding temperature of about 380° C., a flow ratio of nitrogen to hydrogen of 1:3, air pressure of 50-130 Pa, and a bias voltage of about 600V are selected to perform the nitriding for about 15-90 min. The cross-section of the stent rod is permeated, that is, except the compound layer on the outermost surface, the interior has a structure as shown in FIG. 2a. The nitrided iron alloy stent after the nitriding treatment is embedded with a resin, and is ground and polished. Results of metallographic observation and hardness test show that the material still remains a deformed structure, and the hardness value is improved to 350HV0.05/10. Another nitrided iron stent sample is taken and polished to a finished size (with a rod width of the stent at 90 μm and a wall thickness of the stent at 50 μm), and measured to have radial strength improved to 130 kPa, over-plasticity still up to 40%, and a corrosion rate during in-vitro soaking improved to 2.25 mm/y.

Embodiment 8

In Step 101, an iron alloy blank is drawn to obtain a lumen stent preform. A 6×0.5 (with an outer diameter of 6 mm and a wall thickness of 0.5 mm) iron alloy tubular blank having a completely annealed structure is used, which has ingredients as follows: C 0.018 wt. %, Si 0.03 wt. %, Mn 0.10 wt.

%, P 0.037 wt. %, S 0.011 wt. %, and Ti 0.30 wt. %, that is, a total alloy element content is 0.496 wt. %, and a content of the strong nitride-forming element Ti is 0.30 wt. %. The iron alloy tubular blank has a hardness of 100HV0.05/10. Further, different hardness can be obtained by changing the alloy ingredients (including the strong nitride-forming element), for example, a hardness range of 100-150HV0.05/10 may also be selected. The completely annealed metallurgical structure is equiaxed grain with a grain size number greater than or equal to 4.

The used drawing passes include: (1) Drawing with a long mandrel by means of a 5 mm external mold and a 4.4 mm mandrel; (2) Drawing with a long mandrel by means of a 4.4 mm external mold and a 4.0 mm mandrel, where an annealing pass may be supplemented after this drawing pass, for example, annealing may be performed for one hour at 650° C. after completion of this drawing; (3) Drawing with a long mandrel by means of a 3.5 mm external mold and a 3.19 mm mandrel; (4) Drawing with a long mandrel by means of a 2.3 mm external mold and a 2.02 mm mandrel; (5) Drawing with a long mandrel by means of a 1.83 mm external mold and a 1.60 mm mandrel; and (6) Drawing without a mandrel by means of a 1.62 mm external mold, where an annealing pass may be supplemented after this drawing pass, for example, annealing may be performed for one hour at 600° C. after completion of this drawing without a mandrel.

In order to reduce generation of drawing defects, elongation coefficients of all the drawing passes should not exceed 2.0, and the elongation coefficients may be selected as about 1.5. Because metal materials have a certain elastic aftereffect, the outer diameter will rebound somewhat after drawing with the 1.62 mm external mold, and the outer diameter is measured to be 1.63 mm and the wall thickness is measured to be 0.095 mm. In order to strictly control quality of the external surface of a tubular product, an allowance of 0.03 mm is reserved for polishing. After mechanical polishing of 0.03 mm, a finished iron alloy tube with the same material as the blank, an outer diameter of 1.6 mm, a wall thickness of 0.080±0.005 mm, hardness of about 120HV0.05/10, and a grain size number greater than or equal to 9, is obtained as a stent preform.

In Step 102, the stent preform manufactured above is cut with laser, at a cutting accuracy of ±5 μm, to obtain a coronary initial stent with a specification of OD 3.0×18 mm. When the stent is expanded to 3.0 mm in diameter, the metal mesh coverage on the surface is about 13%. The laser-cut iron alloy initial stent is polished to a finished size (with a rod width of the stent at 90 μm and a wall thickness of the stent at 50 μm), and measured to have radial strength of 37 kPa, a corrosion rate during in-vitro soaking of 1.0 mm/y, and over-plasticity of 50%.

In Step 103, after rough polishing and cleaning, the laser-cut initial stent is placed into a glow plasma furnace for nitriding treatment. A nitriding temperature of about 530° C., a flow ratio of nitrogen to hydrogen of 1:3, air pressure of 200-300 Pa, and a bias voltage of about 700V are selected to perform the nitriding for about 90-150 min. The cross-section of the stent rod is permeated, that is, except the compound layer on the outermost surface, the interior has a structure as shown in FIG. 2*a*. The nitrided iron alloy stent after the nitriding treatment is embedded with a resin, and is ground and polished. Results of metallographic observation and hardness test show that the grain size number of the material is still greater than or equal to 9, and the hardness value is improved to 350HV0.05/10. Another nitrided iron stent sample is taken and polished to a finished size (with a rod width of the stent at 90 μm and a wall thickness of the stent at 50 μm), and measured to have radial strength improved to 130 kPa, over-plasticity still up to 40%, and a corrosion rate during in-vitro soaking improved to 2.25 mm/y.

COMPARATIVE EXAMPLE

In Step 101, a blank is drawn to obtain a lumen stent preform. A 6×0.5 (with an outer diameter of 6 mm and a wall thickness of 0.5 mm) pure iron tubular blank having a completely annealed structure is used (a total impurity element content is less than or equal to 0.5 wt. %, where a carbon content is less than or equal to 0.022%). The pure iron tubular blank has a hardness of about 90HV0.05/10, and the metallurgical structure of the completely annealed structure is equiaxed grain with a grain size number greater than or equal to 4.

Drawing passes that can be used include: (I) Drawing with a long mandrel by means of a 5 mm external mold and a 4.4 mm mandrel; (2) Drawing with a long mandrel by means of a 4.4 mm external mold and a 4.0 mm mandrel, where an annealing pass may be supplemented after this drawing pass, for example, annealing may be performed for half an hour at 650° C. after completion of this drawing; (3) Drawing with a long mandrel by means of a 3.5 mm external mold and a 3.19 mm mandrel; (4) Drawing with a long mandrel by means of a 2.3 mm external mold and a 2.02 mm mandrel; (5) Drawing with a long mandrel by means of a 1.83 mm external mold and a 1.60 mm mandrel; and (6) Drawing without a mandrel by means of a 1.62 mm external mold, where an annealing pass may be supplemented after the drawing without a mandrel, for example, annealing may be performed for 1 hour at 570° C. after completion of this drawing without a mandrel, to complete the whole drawing process.

In order to reduce generation of drawing defects, elongation coefficients of all the drawing passes should not exceed 2.0, and the elongation coefficients may be selected as about 1.5. Because metal materials have a certain elastic aftereffect, the outer diameter will rebound somewhat after drawing with the 1.62 mm external mold, and the outer diameter is measured to be 1.63 mm and the wall thickness is measured to be 0.095 mm. In order to strictly control quality of the external surface of a tubular product, an allowance of 0.03 mm is reserved for polishing. After mechanical polishing of 0.03 mm, a finished pure iron tube with unchanged ingredients (a total impurity element content is less than or equal to 0.5 wt. %, where a carbon content is less than or equal to 0.022%), an outer diameter of 1.60 mm, a wall thickness of 0.080±0.005 mm, hardness of about 90HV0.05/10, and a grain size number of 6, is obtained as a stent preform.

In Step 102, the stent preform manufactured above is cut with laser, at a cutting accuracy of ±5 μm, to obtain a coronary initial stent with a specification of OD 3.0×18 mm. The laser-cut initial stent is polished to a finished size (with a rod width of the stent at 90 μm and a wall thickness of the stent at 50 μm), and measured to have radial strength of 30 kPa, a corrosion rate during in-vitro soaking of 0.9, mm/y and over-plasticity of 50%.

In Step 103, after rough polishing and cleaning, the laser-cut initial stent is placed into a glow plasma furnace for nitriding treatment. A nitriding temperature of about 320° C., a flow ratio of nitrogen to hydrogen of 1:3, air pressure of 380-500 Pa, and a bias voltage of about 700V are selected to perform the nitriding for about 90-150 min. The length of the nitriding time is determined collectively by the sizes (for example, wall thickness) of the medical instrument and members thereof, penetration depth in need of control, and the nitriding temperature. The nitriding time given in the embodiments is the time for the cross-section of the stent rod to be penetrated through (the single diffusion layer runs through the wall thickness direction of the whole stent rod, except the compound layer on the outermost surface), at a size of the iron tube addressed in this embodiment. The nitrided lumen stent after the nitriding treatment is embedded with a resin, and is ground and polished. Results of metallographic observation and hardness test show that the material still remains a deformed structure, and the hardness value is improved to 120HV0.05/10. Another nitrided iron stent sample is taken and polished to a finished size (with a rod width of the stent at 90 μm and a wall thickness of the stent at 50 μm), and measured to have radial strength of 37 kPa, over-plasticity maintained at 50%, and a corrosion rate during in-vitro soaking remained at 0.9 mm/y.

In the above comparative example, for the pure iron tubular blank, an annealing pass is further supplemented after completion of the drawing pass without a mandrel in the drawing, to manufacture a lumen stent preform with hardness of only about 90HV0.05/10 and a grain size number of 6, where the hardness is not within a range of 160-250HV0.05/10 as required for the lumen stent prepared in the present invention, and the grain size number is less than at least 9 as required by the present invention. The modification effect obtained by subjecting the lumen stent preform to plasma nitriding is not obvious. For example, after the plasma nitriding, the radial strength is improved from 30 kPa only to 37 kPa, the hardness is improved from 90HV0.05/10 only to 120HV0.05/10, and the corrosion rate during in-vitro soaking and the over-plasticity remain unchanged, so that the above radial strength fails to meet the requirements for the lumen stent.

Embodiment 3 of the present invention is taken as an example to be compared with the comparative example. In Embodiment 3, the same pure iron tubular blank is used, the drawing possess is changed, the annealing treatment is no longer performed after the drawing without a mandrel, and the deformed structure formed in the drawing is remained. Therefore a lumen stent preform with hardness of about 250HV0.05/10 and a deformed structure after cold machining can be manufactured by drawing. After plasma nitriding, the radial strength can be improved from 90 kPa to 110 kPa, the hardness is improved to 300HV0.05/10, the corrosion rate during in-vitro soaking is doubled, and the over-plasticity is maintained unchanged and can still reach 35%, so that requirements for the radial strength and plasticity of a conventional lumen stent is met.

It can be seen from the above that, in the present invention, a blank made of a material of pure iron or an iron alloy containing no strong nitride-forming element can be drawn, by a drawing process, into an iron-based lumen stent preform with hardness of 160-250HV0.05/10 and a microstructure that is a deformed structure having a grain size number greater than or equal to 9 or a deformed structure after cold machining; or an iron alloy lumen stent preform with a microstructure that is a deformed structure has a grain size number greater than or equal to 9 or a deformed structure after cold machining and contains a strong nitride-forming element is manufactured. The preform can enable implementation of plasma nitriding within a wider temperature range (320-560° C.), and at the same time the lumen stent manufactured therefrom has a hardness of 250-350HV0.05/10 and over-plasticity of 20-50%. For a coronary stent with a wall thickness within a range of 40-150 μm, metal coverage of 11-16%, and an OD of 2-5.0 mm, the radial strength is 80-260 kPa; and for a peripheral stent with a wall thickness within a range of 90-200 μm, metal coverage of 7-11%, and an OD of 5.0-14 mm, the radial strength can reach 50-130 kPa, so that requirements for mechanical properties of a conventional lumen stent is met.

In some particular embodiments of the present invention, lumen stent preforms suitable for low-temperature (320-420° C.) plasma nitriding, with hardness of 200-250HV0.05/10 and a microstructure that is a deformed structure after cold machining, are prepared by a drawing process, and the influences of the side effects of reversion and/or recrystallization caused by a temperature set too high in the nitriding procedure are reduced. The lumen stent manufactured therefrom has hardness that can reach 300-350HV0.05/10, and over-plasticity of 20-40%. For a coronary stent with a wall thickness within a range of 40-150 μm, metal coverage of 11-16%, and an OD of 2-5.0 mm, the radial strength is 80-260 kPa; and for a peripheral stent with a wall thickness within a range of 90-200 μm, metal coverage of 7-11%, and an OD of 5.0-14 mm, the radial strength can reach 85 kPa or even higher, so that requirements for mechanical properties of a conventional lumen stent are still met.

It should be understood that, the above data are numerical values in particular examples of the present invention that are adjusted according to different specifications of particular products, and thus only serve as examples, instead of limitation on the present invention. Lumen stent preforms and lumen stents manufactured by those of ordinary skill in the art based on the teachings of the present invention, as well as the preparation methods employed of the above two all fall within the protection scope of the present invention.

The invention claimed is:

1. A lumen stent preform, characterized in that the lumen stent preform is pure iron or an iron alloy, a total impurity element content of the pure iron is less than or equal to 0.5 wt. %, a total alloy element content of the iron alloy is less than or equal to 3 wt. %, and the iron alloy contains no strong nitride-forming element, the lumen stent preform has a hardness of 160-250HV0.05/10, and has a microstructure that is a deformed structure having a deformed structure after cold machining, wherein a carbon content in the total alloy elements of the iron alloy is less than or equal to 0.45 wt. %.

2. The lumen stent preform according to claim 1, characterized in that the lumen stent preform has a hardness of 200-250HV0.05/10, and has a microstructure that is a deformed structure after cold machining.

3. The lumen stent preform according to claim 1, characterized in that a carbon content in the total impurity elements of the pure iron is less than or equal to 0.022%.

4. The lumen stent preform according to claim 1, characterized in that the lumen stent preform has an outer diameter of 1.2-4.2 mm and a wall thickness of 0.08-0.24 mm.

5. The lumen stent preform according to claim 1, characterized in that the alloy elements in the iron alloy include: C 0.3 wt. %, Si 0.30 wt. %, Mn 0.60 wt. %, P 0.025 wt. %, S 0.025 wt. %, Ni 0.25 wt. %, Cu 0.25 wt. %; or, the alloy elements in the iron alloy include: C 0.4 wt. %, Si 0.40 wt. %, Mn 0.65 wt. %, P 0.04 wt. %, S 0.04 wt. %, Ni 0.5 wt. %, Cu 0.5 wt. %.

6. The lumen stent preform according to claim 1, characterized in that the lumen stent preform is obtained by drawing a pure iron blank or an iron alloy blank, and the pure iron blank and the iron alloy blank are incompletely annealed structure or completely annealed structure.

7. The lumen stent preform according to claim 6, characterized in that:
   when the pure iron blank and the iron alloy blank are both incompletely annealed structure, the hardness of the pure iron blank is greater than 90HV0.05/10, the hardness of the iron alloy blank is greater than 110HV0.05/10, and the microstructures of the pure iron blank and the iron alloy blank are deformed structures; and
   when both the pure iron blank and the iron alloy blank are completely annealed structure, the hardness of the pure iron blank is 90HV0.05/10, the hardness of the iron alloy blank is 100-150HV0.05/10, and the microstructures are both equiaxed grains with a grain size scale greater than or equal to 4.

8. The lumen stent preform according to claim 6, characterized in that:
   when the pure iron blank and the iron alloy blank are both incompletely annealed structure, the walls of the pure iron blank and the iron alloy blank are not completely annealed, the wall thickness is 0.13-3 mm, and the outer diameter is 2.3-20 mm; and
   when the pure iron blank and the iron alloy blank are both completely annealed structure, the wall thickness of the pure iron blank and the iron alloy blank is 0.16-3 mm, and the outer diameter is 3.5~20 mm.

9. A lumen stent preform, characterized in that the lumen stent preform is pure iron or an iron alloy, a total impurity element content of the pure iron is less than or equal to 0.5 wt. %, a total alloy element content of the iron alloy is less than or equal to 3 wt. %, and the iron alloy contains no strong nitride-forming element, the lumen stent preform has a hardness of 160-250HV0.05/10, and has a microstructure that is a deformed structure having a grain size scale greater than or equal to 9.

10. The lumen stent preform according to claim 9, characterized in that the lumen stent preform has a hardness of 200-250HV0.05/10, and has a microstructure that is a deformed structure after cold machining, and wherein a carbon content in the total impurity elements of the pure iron is less than or equal to 0.022%, and a carbon content in the total alloy elements of the iron alloy is less than or equal to 0.45 wt. %.

11. The lumen stent preform according to claim 9, characterized in that the lumen stent preform has an outer diameter of 1.2-4.2 mm and a wall thickness of 0.08-0.24 mm.

12. The lumen stent preform according to claim 9, characterized in that the lumen stent preform is obtained by drawing a pure iron blank or an iron alloy blank, and the pure iron blank and the iron alloy blank are incompletely annealed structure or completely annealed structure.

13. The lumen stent preform according to claim 12, characterized in that:
   when the pure iron blank and the iron alloy blank are both incompletely annealed structure, the hardness of the pure iron blank is greater than 90HV0.05/10, the hardness of the iron alloy blank is greater than 110HV0.05/10, and the microstructures of the pure iron blank and the iron alloy blank are deformed structures; and
   when both the pure iron blank and the iron alloy blank are completely annealed structure, the hardness of the pure iron blank is 90HV0.05/10, the hardness of the iron alloy blank is 100-150HV0.05/10, and the microstructures are both equiaxed grains with a grain size scale greater than or equal to 4.

14. The lumen stent preform according to claim 12, characterized in that:
   when the pure iron blank and the iron alloy blank are both incompletely annealed structure, the walls of the pure iron blank and the iron alloy blank are not completely annealed, the wall thickness is 0.13-3 mm, and the outer diameter is 2.3-20 mm; and
   when the pure iron blank and the iron alloy blank are both completely annealed structure, the wall thickness of the pure iron blank and the iron alloy blank is 0.16-3 mm, and the outer diameter is 3.5~20 mm.

15. The lumen stent preform according to claim 9, characterized in that the alloy elements in the iron alloy include: C 0.3 wt. %, Si 0.30 wt. %, Mn 0.60 wt. %, P 0.025 wt. %, S 0.025 wt. %, Ni 0.25 wt. %, Cu 0.25 wt. %; or, the alloy elements in the iron alloy include: C 0.4 wt. %, Si 0.40 wt. %, Mn 0.65 wt. %, P 0.04 wt. %, S 0.04 wt. %, Ni 0.5 wt. %, Cu 0.5 wt. %.

16. A lumen stent preform, characterized in that the lumen stent preform is pure iron or an iron alloy, a total impurity element content of the pure iron is less than or equal to 0.5 wt. %, a total alloy element content of the iron alloy is less than or equal to 3 wt. %, and the iron alloy contains no strong nitride-forming element, the lumen stent preform has a hardness of 160-250HV0.05/10, and has a microstructure that is a deformed structure having a grain size scale greater than or equal to 9 or a deformed structure after cold machining;
   wherein the lumen stent preform is obtained by drawing a pure iron blank or an iron alloy blank, and the pure iron blank and the iron alloy blank are incompletely annealed structure or completely annealed structure;
   wherein when the pure iron blank and the iron alloy blank are both incompletely annealed structure, the hardness of the pure iron blank is greater than 90HV0.05/10, the hardness of the iron alloy blank is greater than 110HV0.05/10, and the microstructures of the pure iron blank and the iron alloy blank are deformed structures; and
   when both the pure iron blank and the iron alloy blank are completely annealed structure, the hardness of the pure iron blank is 90HV0.05/10, the hardness of the iron alloy blank is 100-150HV0.05/10, and the microstructures are both equiaxed grains with a grain size scale greater than or equal to 4.

17. The lumen stent preform according to claim 16, characterized in that the lumen stent preform has a hardness of 200-250HV0.05/10, and has a microstructure that is a deformed structure after cold machining.

18. The lumen stent preform according to claim 16, characterized in that a carbon content in the total impurity elements of the pure iron is less than or equal to 0.022%, and a carbon content in the total alloy elements of the iron alloy is less than or equal to 0.45 wt. %.

19. The lumen stent preform according to claim 16, characterized in that the alloy elements in the iron alloy include: C 0.3 wt. %, Si 0.30 wt. %, Mn 0.60 wt. %, P 0.025 wt. %, S 0.025 wt. %, Ni 0.25 wt. %, Cu 0.25 wt. %; or, the alloy elements in the iron alloy include: C 0.4 wt. %, Si 0.40 wt. %, Mn 0.65 wt. %, P 0.04 wt. %, S 0.04 wt. %, Ni 0.5 wt. %, Cu 0.5 wt. %.

20. The lumen stent preform according to claim 16, characterized in that:
   when the pure iron blank and the iron alloy blank are both incompletely annealed structure, the walls of the pure iron blank and the iron alloy blank are not completely annealed, the wall thickness is 0.13-3 mm, and the outer diameter is 2.3-20 mm; and when the pure iron blank and the iron alloy blank are both completely annealed structure, the wall thickness of the pure iron blank and the iron alloy blank is 0.16-3 mm, and the outer diameter is 3.5~20 mm.

* * * * *